(12) United States Patent
Tominaga et al.

(10) Patent No.: US 10,401,322 B2
(45) Date of Patent: Sep. 3, 2019

(54) BIOMOLECULE ANALYZER

(71) Applicant: Merck Ltd., Tokyo (JP)

(72) Inventors: Taiga Tominaga, Sakai (JP); Hideki Kinoshita, Sakai (JP); Shinichi Goto, Sakai (JP); Mieko Hirabayashi, Sakai (JP); Kouhei Kageyama, Sakai (JP); Takateru Matsunaga, Sakai (JP); Kimihiko Yabe, Sakai (JP)

(73) Assignee: Merck LTD., Tokyo (JP)

( * ) Notice: Subject to any disclaimer, the term of this patent is extended or adjusted under 35 U.S.C. 154(b) by 0 days.

(21) Appl. No.: 15/303,555

(22) PCT Filed: Dec. 8, 2015

(86) PCT No.: PCT/JP2015/084445
§ 371 (c)(1),
(2) Date: Oct. 12, 2016

(87) PCT Pub. No.: WO2016/098648
PCT Pub. Date: Jun. 23, 2016

(65) Prior Publication Data
US 2017/0276644 A1    Sep. 28, 2017

(30) Foreign Application Priority Data

Dec. 17, 2014 (JP) .................. 2014-255113
Feb. 24, 2015 (JP) .................. 2015-034588

(51) Int. Cl.
*G01N 27/453* (2006.01)
*G01N 27/447* (2006.01)

(52) U.S. Cl.
CPC ............ *G01N 27/44739* (2013.01);
*G01N 27/44773* (2013.01)

(58) Field of Classification Search
CPC .......... G01N 27/44739; G01N 27/453; G01N 27/44704

See application file for complete search history.

(56) References Cited

U.S. PATENT DOCUMENTS 3,208,929 A * 9/1965 Raymond ........ G01N 27/44756
204/618
4,574,040 A * 3/1986 Delony ............ G01N 27/44756
204/606

(Continued)

FOREIGN PATENT DOCUMENTS

EP    0 382 426 A2    8/1990
GB    2169703 A    7/1986

(Continued)

OTHER PUBLICATIONS

Official Communication issued in International Patent Application No. PCT/JP2015/084445, dated Feb. 23, 2016.

*Primary Examiner* — Alexander S Noguerola
(74) *Attorney, Agent, or Firm* — David J. Wilson

(57) ABSTRACT

A separation unit is a configuration that is arranged vertically, and thus bubbles generating from the electrode will not negatively influence the contact location between the transfer membrane and separation unit. An anode (32) is arranged at a position separated by a certain distance in the conveying direction (X) of the transfer membrane (1) from the dispensing part (50a) of an electrophoresis gel chip (50). An insulating electrode cover (35) for setting free bubbles generating from the anode (32) is arranged at an upper part of the anode (32).

19 Claims, 13 Drawing Sheets

(56) References Cited

U.S. PATENT DOCUMENTS

| | | | | |
|---|---|---|---|---|
| 4,631,120 A | * | 12/1986 | Pohl | G01N 27/44717 |
| | | | | 204/465 |
| 4,715,942 A | * | 12/1987 | Tezuka | G01N 27/44756 |
| | | | | 204/618 |
| 4,747,918 A | * | 5/1988 | Wassenberg, II | G01N 27/4473 |
| | | | | 204/462 |
| 4,889,606 A | * | 12/1989 | Dyson | G01N 27/4473 |
| | | | | 204/464 |
| 4,994,166 A | | 2/1991 | Fernwood et al. | |
| 5,047,135 A | * | 9/1991 | Nieman | G01N 27/44782 |
| | | | | 204/619 |
| 5,234,559 A | | 8/1993 | Collier et al. | |
| 5,306,403 A | | 4/1994 | Vo-Dinh | |
| 5,433,837 A | | 7/1995 | Brunk et al. | |
| 5,916,429 A | | 6/1999 | Brunk | |
| 7,960,184 B2 | * | 6/2011 | Morozov | G01N 33/561 |
| | | | | 422/553 |
| 2001/0015320 A1 | * | 8/2001 | Anderson | G01N 27/44773 |
| | | | | 204/606 |
| 2008/0202935 A1 | * | 8/2008 | Cheung | G01N 27/44704 |
| | | | | 204/618 |
| 2009/0127118 A1 | | 5/2009 | Unuma et al. | |
| 2011/0094887 A1 | | 4/2011 | Midorikawa et al. | |
| 2017/0276644 A1 | * | 9/2017 | Tominaga | G01N 27/44773 |

FOREIGN PATENT DOCUMENTS

| | | |
|---|---|---|
| JP | 59-194050 U | 12/1984 |
| JP | 01-112147 A | 4/1989 |
| JP | 03-115850 A | 5/1991 |
| JP | 09-501774 A | 2/1997 |
| JP | 2006-162445 A | 6/2006 |
| JP | 2007-292616 A | 11/2007 |
| WO | 2010/001675 A1 | 1/2010 |

\* cited by examiner

BIOMOLECULE ANALYZER

TECHNICAL FIELD

The present relates to a biomolecule analyzer for analyzing biomolecules such as proteins.

BACKGROUND ART

In proteome analysis, which bears a central position in post-genomic research, a combination of two-dimensional electrophoresis (2DE) and Western blotting has been known as an excellent separation analytical method. 2DE can separate proteomes with high resolution into a plurality of components (proteins), based on two independent physical properties unique to proteins (electric charge and molecular weight) using various separation media. In the case of further analyzing proteins using the separation results by 2DE, it is preferable to fixate the plurality of proteins contained in the separation medium on a transfer membrane by way of the Western blotting. This is because analysis is easy, since the proteins fixed to the transfer membrane can be stably kept over a long period. In particular, in the case of comprehensively comparing and reviewing a plurality of biological properties of proteins like the fluctuations in expression of proteins and existence of post-translational modification using the separation results by 2DE, Western blotting is considered an essential process.

In conventional Western blotting, there is a problem in that the patterns of proteins fixed to the transfer membrane blurs and warps due to bubbles generating from the anode adhering at the contact location between the transfer membrane and separation medium. To address this problem, Patent Document 1 discloses a scheme using a columnar anode coated with a porous material. Patent Document 1 discloses the advantage of this scheme as follows. Upon bubbles generating from the anode passing through the porous material, since the sizes thereof become large, the bubbles tend to rise to the water surface. Since it is thereby possible to prevent mixing of microscopic bubbles into the buffer, the negative influence of bubbles on the contact location can be eliminated.

Patent Document 1: U.S. Pat. No. 5,916,429 (issued Jun. 29, 1999)

Patent Document 2: U.S. Pat. No. 5,234,559 (issued Aug. 10, 1993)

Patent Document 3: Japanese Published Translation of PCT International Publication for Patent Applications "Japanese Unexamined Patent Application (Translation of PCT Publication), Publication No. H9-501774 (published Feb. 18, 1997)"

DISCLOSURE OF THE INVENTION

Problems to be Solved by the Invention

With the technology of Patent Document 1, since the formed bubbles are collectively released from the upper part of the buffer tank, a case of installing the separation medium horizontally is effective. However, in the case of installing the separation medium vertically, since the bubbles generating from the anode head towards the contact location between the transfer membrane and separation medium before reaching the liquid surface, the problem of bubbles negatively influencing the contact location still arises as a result.

The present invention has been made in order to solve the above-mentioned problem. Further, an object thereof is to provide a biomolecule analyzer that is a configuration in which the separation unit is arranged vertically, and bubbles generating from the electrode do not negatively influence the contact location between the transfer membrane and separation unit.

Means for Solving the Problems

The biomolecule analyzer according to an embodiment of the present invention
 a transfer membrane;
 a conveying unit that conveys the transfer membrane along a predetermined conveying direction;
 a separation unit that perpendicularly abuts the transfer membrane and is installed vertically, separates analyte by way of electrophoresis, and dispenses the analyte that has been separated to the transfer membrane;
 an electrode that is disposed at a position separated by a certain distance in the conveying direction from a contact location between the separation unit and the transfer membrane; and
 an insulating electrode cover that is disposed at an upper part of the electrode to abut the electrode or be separated from the electrode.

In addition, in order to solve the above-mentioned problem, a biomolecule analyzer according to an aspect of the present invention includes:
 a buffer solution tank;
 a transfer membrane that is disposed inside the buffer solution tank;
 a conveying unit that conveys the transfer membrane along a predetermined conveying direction;
 a separation unit that perpendicularly abuts the transfer membrane and is installed vertically, separates analyte by way of electrophoresis, and dispenses the analyte that has been separated to the transfer membrane;
 an electrode that is disposed at a position separated by a certain distance in the conveying direction from a contact location between the separation unit and the transfer membrane; and
 an insulating electrode cover that is disposed between the electrode and the contact location,
 in which a first concave part is provided at a position on a bottom part of the buffer solution tank that is interposed by the electrode and the contact location, and
 in which the electrode cover hangs down towards the first concave part.

Effects of the Invention

According to an aspect of the present invention, the effect is exerted of being able to provide a biomolecule analyzer that is a configuration in which the separation unit is arranged vertically, and thus bubbles generating from the electrode will not negatively influence the contact location between the transfer membrane and separation unit.

PREFERRED MODE FOR CARRYING OUT THE INVENTION

First Embodiment

A first embodiment according to the present invention will be explained hereinafter based on FIGS. 1 to 4.

(Framed Transfer Membrane 10)

Figure 2A:
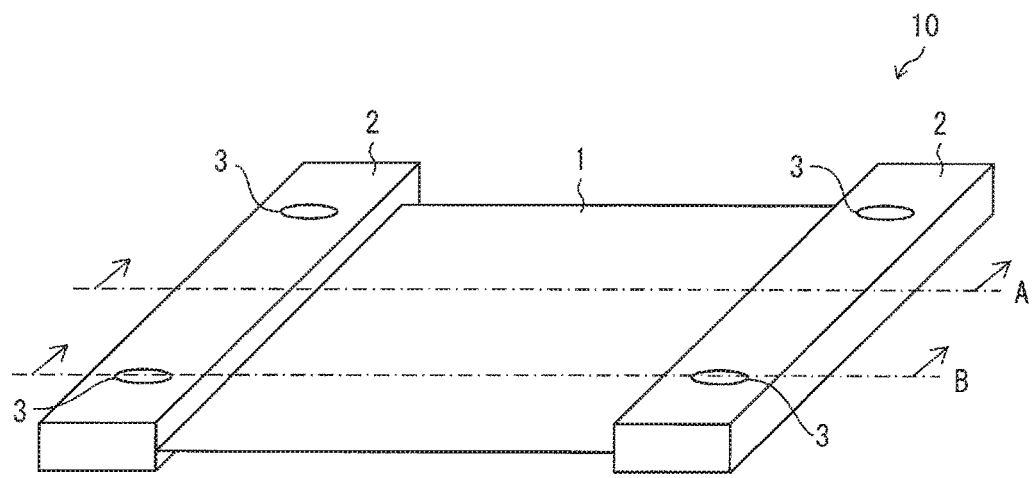
FIG. 2 is a view illustrating an outline of a framed transfer membrane according to the first embodiment of the present invention.
Figure 2B:
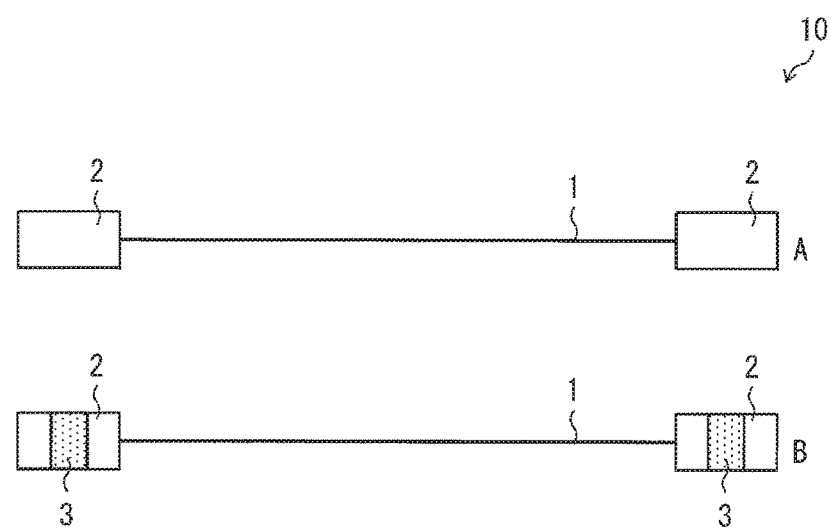

First, a framed transfer membrane used in the biomolecule analyzer according to the present embodiment will be explained hereinafter by referencing FIG. 2. FIG. 2(a) is a view illustrating an outline of a framed transfer membrane 10. FIG. 2(b) provides cross-sectional views along line A and line B in FIG. 2(a).

As shown in FIG. 2(a), the framed transfer membrane 10 is supported with one side of the transfer membrane 1 (first side) and one side opposing this side (second side) independently by a pair of frames (frame members) 2.

As shown in the cross-sectional views on line A and line B in FIG. 2(b), the framed transfer membrane 10 more preferably is provided with fitting parts (through holes) of open form through which the frame 2 passes, as fitting parts 3 of the pair of frames 2. The fitting parts 3 can each fit to fitting parts of a corresponding convex-type shape. It is thereby possible to fix the framed transfer membrane 10 and biomolecule analyzer with the fitting parts 3.

The framed transfer membrane 10 can tighten the transfer membrane 1 without slack by horizontally fixing the pair of frames 2 to be separated from each other. In addition, since it is possible to fix the transfer membrane 1 which is sectioned into a predetermined shape in advance by the frame 2, the framed transfer membrane 10 can be installed in the biomolecule analyzer while imparting easy and appropriate tension to the transfer membrane 1. For this reason, it is possible to prevent warping of the blot when fixing to the biomolecule analyzer and transferring analyte by direct blotting.

In addition, with the framed transfer membrane 10, it is possible to use the frame 2 as a sinker of the transfer membrane 1. For this reason, it is possible to prevent the transfer membrane 1 in the reagent from moving inside a reagent tank such as a shaker, and irregularity arising in the antibody response. Furthermore, the framed transfer membrane 10 is a simple configuration consisting of the transfer membrane 1 and pair of frames 2; therefore, compared with one that broadly fixes the transfer membrane smoothly by fixing the entire periphery by a frame, and one that broadly fixes the transfer membrane by a curved frame, it is not bulky and, for example, it is possible to reduce the amount of antibody used when performing Western blotting.

(Transfer Membrane 1)

The transfer membrane 1 is a membrane for adsorbing and retaining biomolecular sample (reagent) separated by the separation unit of the biomolecule analyzer. Herein, it is preferable for the transfer membrane 1 to be able to stably preserve a biomolecular sample (analyte) separated by the separation unit over a long period, and further, and to be an absorbing/retaining body of biomolecular samples that facilitates subsequent analysis. As the material of the transfer membrane 1, it is preferably a material having high strength, and having high sample binding capacity (adsorbable weight per unit volume). As the transfer membrane 1, a polyvinylidene fluoride (PVDF) membrane or the like is suited in the case of the sample being protein. It should be noted that it is preferable to perform hydrophilization treatment using methanol or the like in advance on the PVDF membrane. Otherwise, a membrane conventionally used in the adsorption of proteins, DNA and nucleic acids such as a nitrocellulose membrane or nylon membrane can also be used.

As the biomolecular samples that can be separated and adsorbed in the biomolecule analyzer, although proteins, DNA and RNA can be exemplified, it is not limited thereto. For example, a preparation from biological material (e.g., cell strain, tissue culture, or tissue fragment), a commercially available reagent, and the like are also included among examples of the sample. Furthermore, polypeptides or polynucleotides are also types of samples.

(Frame 2)

For each of the pair of frames 2, the length of the frame 2 is sufficient if longer than the length of one side of the transfer membrane 1 to be fixed. In addition, the frame 2 preferably consists of an insulating material. As the insulating material, it is possible to use a resin such as polymethylmethacrylate (acrylic), polystyrene, polyethylene, polypropylene, polyethylene terephthalate (PET), polyacetal (POM) and polyether ether ketone (PEEK), or glass.

In addition, hydrophilization treatment is more preferably conducted on the surface of the frame 2. For example, a coating layer may be provided to the surface of the frame 2 consisting of the above-mentioned materials. It is thereby possible to prevent a reagent such as protein dispensed from the dispensing part of the separation unit from adhering to the surface of the frame 2, and possible to prevent the frame 2 from being contaminated.

It should be noted that the water contact angle to the surface of the frame 2 is preferably no more than 90°, and more preferably no more than 60°. By establishing the water contact angle to the surface of the frame 2 as no more than 90°, it is possible to suitably prevent the frame 2 from being contaminated by reagent.

(Biomolecule Analyzer 200)

Figure 3:
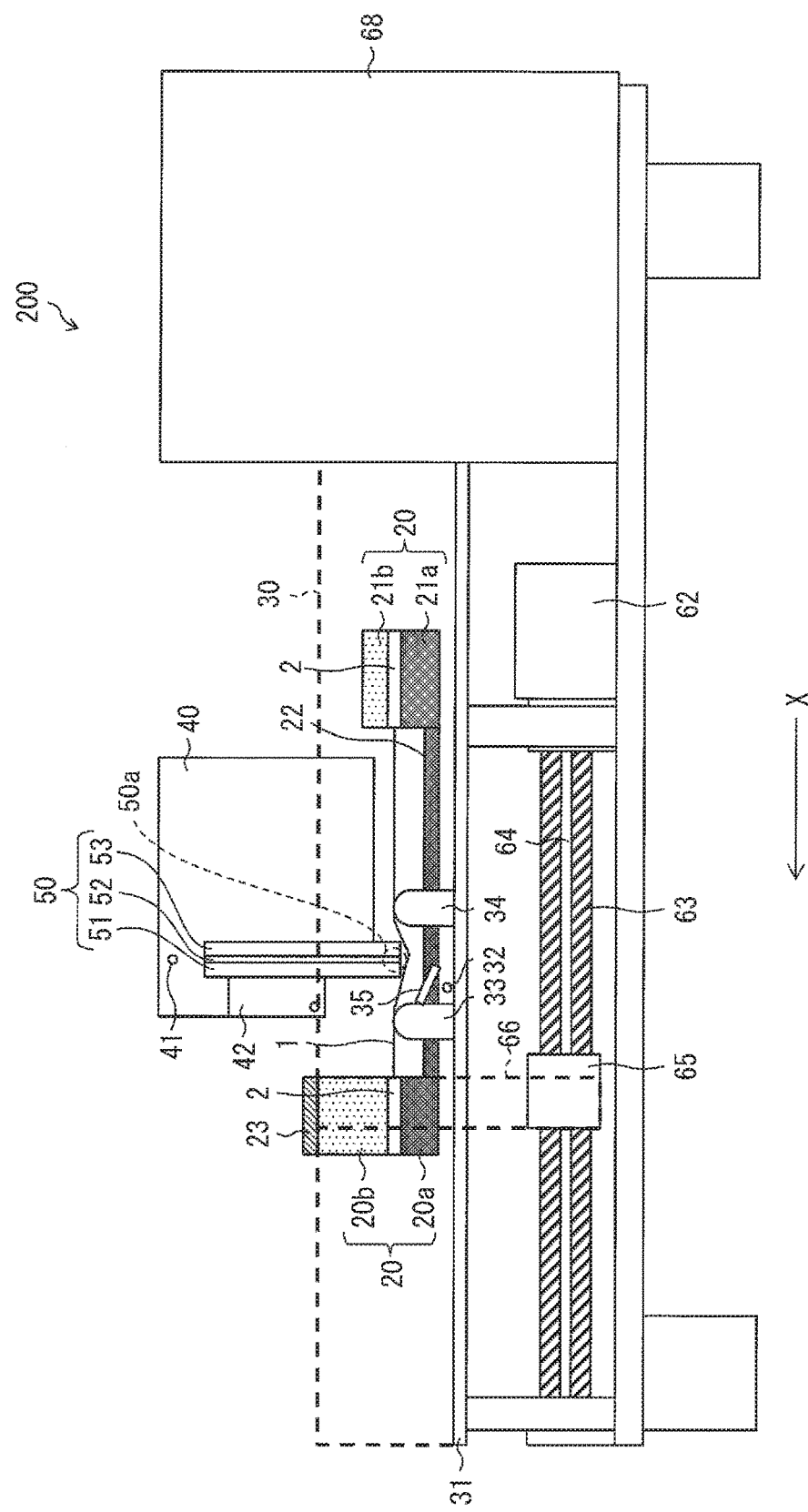
FIG. 3 is a view illustrating an outline of the biomolecule analyzer according to an embodiment of the present invention.

Next, a biomolecule analyzer 200 according to an embodiment of the present invention will be explained in detail by referencing FIG. 3. FIG. 3 is a view illustrating an outline of the biomolecule analyzer 200 according to the embodiment of the present invention. As shown in this figure, the biomolecule analyzer 200 includes a clamp 20, an anode buffer tank 30 (buffer tank), an anode stage 31, a cathode buffer tank 40, an electrophoresis gel chip 50 (separation unit) and a conveying part.

In the biomolecule analyzer 200, the anode buffer tank 30 is fixed in a removable state relative to the anode stage 31. The clamp 20 is arranged inside the anode buffer tank 30, and the framed transfer membrane 10 is fixed to the clamp 20 inside of the anode buffer tank 30. The cathode buffer tank 40 is fixed in a removable state relative to the anode buffer tank 30. The electrophoresis gel chip 50 is arranged in the biomolecule analyzer 200 so that, among both end parts opposing each other, one end part is positioned inside of the anode buffer tank 30, and the other end part is positioned inside of the cathode buffer tank 40.

An overview of the biomolecule analyzer 200 is as follows. The electrophoresis gel chip 50 separates the analyte introduced to the separation gel 52 by way of electrophoresis, and dispenses the separated analyte through a dispensing part 50a, which is at one end of the electrophoresis gel chip 50, onto the transfer membrane 1. The conveying part conveys the transfer membrane 1 in a conveying direction X (direction from a side (first side) at which the frame 2 of the framed transfer membrane 10 is provided towards another side (second side) at which the frame 2 is provided). The dispensed analyte is thereby adsorbed at a position according to the timing at which dispensed on the transfer membrane 1 (position opposing the electrophoresis gel chip 50 at the timing dispensed). The separated analyte is thereby transferred to the transfer membrane 1.

(Clamp 20)

As shown in FIG. 3, the clamp 20 includes front clamps 20a and 20b, rear clamps 21a and 21b, and a clamp frame 22. The front clamps 20a and 20b are arranged at a conveying end point side upon the transfer membrane 1 being delivered, while the rear clamps 21a and 21b are arranged at a conveying starting point side.

In the clamp 20, the front clamp 20a and front clamp 20b are fixed so as to be able to release by a jig. Fitting parts (not illustrated) are provided at two locations on the front clamp 20a, and relative to these fitting parts, the fitting parts 3 provided at two locations on one frame 2 shown in FIG. 2(a) are respectively fitted. Subsequently, one frame 2 is inserted between and fixed by the front clamp 20a and front clamp 20b.

Similarly, in the clamp 20, the rear clamp 21a and rear clamp 21b are fixed so as to be able to release by a jig. Fitting parts (not illustrated) are provided at two locations on the rear clamp 21a, and relative to these fitting parts, the fitting parts 3 provided at two locations on the other frame 2 shown in FIG. 2(a) are respectively fitted. Subsequently, the other frame 2 is inserted between and fixed by the rear clamp 21a and rear clamp 21b.

The clamp frame 22 fixes the front clamp 20a and rear clamp 21a in a state isolating by a certain distance. For this reason, when fixing the framed transfer membrane 10 by way of the clamp 20, the transfer membrane 1 is fixed in a state tightened without slack. Furthermore, the clamp frame 22 fixes the front clamp 20a and rear clamp 21b from a lateral side to the conveying direction of the transfer membrane 1 (outer side of two sides not supported by the frames 2). When fixing the framed transfer membrane 10 to the biomolecule analyzer 200 through the clamp 20, it is thereby possible to arrange the framed transfer membrane 10 so that the clamp frame 22 does not contact the electrophoresis gel chip 50 as well as guides 33 and 34 in the conveying path of the transfer membrane 1.

A carrier 23 is provided to the front clamp 20b. When installing the clamp 20 to an inner side of the anode buffer tank 30, the clamp 20 can be fixed in a removable state to a guide pole 66 arranged at an outer side of the anode buffer tank 30 via the carrier 23.

(Anode Buffer Tank 30)

In FIG. 3, the anode buffer tank 30 is shown with a dotted line. As shown in FIG. 3, the anode buffer tank 30 includes an anode (electrode) 32, guides (support members) 33 and 34, as well as an anode cover 35 (electrode cover).

Anode buffer is filled in the anode buffer tank 30. As the anode buffer, for example, it is possible to use buffer solutions such as a Tris/glycine-based buffer solution, acetic acid buffer solution, sodium carbonate-based buffer solution, CPS buffer solution, Tris/boric acid/EDTA buffer solution, Tris/acetic acid/EDTA buffer solution, MOPS, phosphoric acid buffer solution, and Tris/tricine-based buffer solution. The framed transfer membrane 10 fixed to the clamp 20 is established in the anode buffer filled inside of the anode buffer tank 30.

The anode 32 is a long and narrow rod-shaped electrode configured from platinum wire or the like. The anode 32 is provided at the bottom of the anode buffer tank 30 so that the length direction thereof is perpendicular to the conveying direction X of the framed transfer membrane 10. The anode 32 is not immediately below the dispensing part 50a of the electrophoresis gel chip 50, but is rather arranged at a position separated by a certain distance from the dispensing part 50a in the conveying direction X. This position is a position that allows for application of a voltage between the anode 32 and cathode 41, from a back face of the transfer membrane 1 on a side opposing the electrophoresis gel chip 50, when the framed transfer membrane 10 is installed.

The guides 33 and 34 are support members that each support a pair of positions interposing from the front/rear in the conveying direction a position on the transfer membrane 1 at which the electrophoresis gel chip 50 abuts (contacts), from the opposite side to the electrophoresis gel chip 50 of the transfer membrane 1. The guides 33 and 34 are provided at the bottom of the anode buffer tank 30, on the conveying path on which the framed transfer membrane 10 is conveyed. The guides 33 and 34 are arranged so that the height direction of each is parallel to the in-plane direction of the electrophoresis gel chip 50, and the framed transfer membrane 10 perpendicularly intersects the conveying direction X in which the framed transfer membrane 10 is delivered. The guides 33 and 34 thereby support the transfer membrane 1 from the back face of the transfer membrane 1 that is a side opposing the electrophoresis gel chip 50, in parallel to the length direction of an end part of the electrophoresis gel chip 50 on a side of the dispensing part 50a.

(Anode Cover 35)

The anode cover 35 is provided to abut the anode 32 or separate from the anode 32 at a top part of the anode 32. Although described later in detail, the biomolecule analyzer 200 can set free bubbles generating from the anode 32 (electrode) to the top part of the anode buffer tank 30 by including the anode cover 35; therefore, it is possible to prevent bubbles from negatively influencing the contact location between the transfer membrane 1 and electrophoresis gel chip 50.

The anode cover 35 is configured from an insulating material. As the insulating material, it is possible to use a resin such as polymethylmethacrylate (acrylic), polystyrene, polyethylene, polypropylene, polyethylene terephthalate (PET), polyacetal (POM) and polyether ether ketone (PEEK), or glass.

In addition, it is more preferable for hydrophilization treatment to be conducted on the surface of the anode cover 35. For example, a coating layer may be provided to the surface of the frame 2 consisting of the above-mentioned material. It is thereby possible to facilitate setting free the bubbles generating from the anode 32 from the top part of the anode buffer tank 30 along the surface of the anode cover 35.

It should be noted that the water contact angle of the surface of the anode cover 35 is preferably no more than 90° C., and more preferably no more than 60°. By establishing the water contact angle of the surface of the anode cover 35 as no more than 90°, it is possible to further facilitate setting free bubbles along the surface of the anode cover 35.

(Cathode Buffer Tank 40)

As shown in FIG. 3, the cathode buffer tank 40 includes a cathode 41 and a lock 42. The cathode 41 is a long and narrow rod-shaped electrode configured from platinum wire or the like. The cathode 41 is arranged at a top part on the inner side of the cathode buffer tank 40 (immediately above the separation gel 52) so that the length direction thereof is orthogonal to the conveying direction of the transfer membrane 1. In other words, the length direction of the cathode 41 is parallel to the length direction of the anode 32.

The cathode buffer is filled into the cathode buffer tank 40. It is possible to use a similar buffer solution to the anode buffer solution as the cathode buffer.

The electrophoresis gel chip 50 is fixed inside of the cathode buffer tank 40 by the lock 42. At this time, the end part of the electrophoresis gel chip 50 on the opposite side to the dispensing part 50a is immersed in the cathode buffer filled in the cathode buffer tank 40. On the other hand, the end part of the electrophoresis gel chip 50 on the side of the dispensing part 50a is immersed in the anode buffer filled in the anode buffer tank 30.

As shown in FIG. 3, the end part of the separation gel 52 on the opposite side to the side of the dispensing part 50a is facing the cathode 41. On the other hand, the end part of the separation gel 52 on the side of the dispensing part 50a is not facing the anode 32. In this way, the end part of the separation gel 52 on the side of the dispensing part 50a is separated by a fixed distance from the anode 32 in the conveying direction of the transfer membrane 1.

(Electrophoresis Gel Chip 50)

As shown in FIG. 3, the electrophoresis gel chip 50 includes an insulating plate 51, separation gel 52 and insulating plate 53. The insulating plate 51 and insulating plate 53, for example, are formed by plates consisting of insulators such as glass and acrylic. The separation gel 52 is formed between the insulating plate 51 and insulating plate 53.

The separation gel 52 is a gel for separating the introduced biomolecule sample (analyte) according to molecular weight. As examples of the separation gel 52, polyacrylamide gel, agarose gel and the like are exemplified, and it is preferable to use a gel made by combining with a buffer solution in the aforementioned suitable compositions. The separation gel 52 can form by filling into the electrophoresis gel chip 50 prior to installing the electrophoresis gel chip 50 to the cathode buffer tank 40.

The electrophoresis gel chip 50 is arranged in the biomolecule analyzer 200 so as to perpendicularly abut against the transfer membrane 1. Furthermore, the electrophoresis gel chip 50 is arranged vertically. The dispensing part 50a of the electrophoresis gel chip 50 contacts the surface of the transfer membrane 1. The biomolecule sample is supplied to the separation gel 52 through the end of the electrophoresis gel chip 50 that is facing the dispensing part 50a and is arranged inside the cathode buffer tank 40. After the biomolecule sample is supplied, electrophoresis is performed by applying a voltage between the anode 32 and cathode 41. As a result thereof, the analyte is transferred to the transfer membrane 1 through the dispensing part 50a.

(Conveying Part)

As shown in FIG. 3, the conveying part includes a motor 62, ball screw 63, guide shaft 64, shaft holder 65, and guide pole 66.

With the conveying part, it is possible to move the shaft holder 65 in the conveying direction X along the guide shaft 64, by causing the ball screw 63 to rotate with the motor 62. The guide pole 66 is fixed to the shaft holder 65, and the guide pole 66 supports the carrier 23 provided to the clamp 20 from outside of the anode buffer tank 30.

The conveying part causes the framed transfer membrane 10 arranged inside of the anode buffer tank 30 to move in the conveying direction via the guide pole 66 arranged outside of the anode buffer tank 30, by causing the motor 62 to rotate according to the above-mentioned configuration.

(Operation of Biomolecule Analyzer 200)

Operation of the biomolecule analyzer 200 will be explained below. First, the framed transfer membrane 10 is fixed by the clamp 20, and arranged at the inner side of the anode buffer tank 30 filled with the anode buffer. The transfer membrane 1 of the framed transfer membrane 10 is fixed in a state supported from the lower side by the guide 33 and guide 34.

Subsequently, the cathode buffer tank 40 to which the electrophoresis gel chip 50 is fixed by the lock 42 is fixed to the top of the anode buffer tank 30. At this time, the cathode buffer tank 40 is installed in a state such that pushes the electrophoresis gel chip 50 to above the transfer membrane 1. The transfer membrane 1 is thereby fixed in a state folded back (valley fold shape) so as to be convex to an opposite side to the electrophoresis gel chip 50 by touching the guide 33, guide 34 and electrophoresis gel chip 50.

Next, by applying a voltage between the anode 32 and cathode 41, the transfer membrane 1 of the framed transfer membrane 10 is conveyed in the transfer direction X shown in FIG. 3, in the state as is transferring the analyte dispensed by the electrophoresis gel chip 50 and pushing against the dispensing part of the electrophoresis gel chip 50, in the anode buffer. For this reason, the tension occurring when the transfer membrane 1 is conveyed is focused on the dispensing part provided at the end of the electrophoresis gel chip 50. In other words, the transfer membrane 1 is conveyed in the transfer direction X while pushing against the dispensing part of the electrophoresis gel chip 50 with a constant force.

For this reason, when conveying the transfer membrane 1 with the framed transfer membrane 10, it is possible to prevent a gap from forming between the transfer membrane 1 and the dispensing part of the analyte of the electrophoresis gel chip 50. Therefore, it is possible to suppress dispersing in the anode buffer prior to the analyte dispensed from the dispensing part of the electrophoresis gel chip 50 being transferred to the transfer membrane 1. It is thereby possible to reduce the fluctuation in the band of analyte transferred to the transfer membrane 1, and it is possible to improve the sensitivity of the biomolecule analyzer.

(Arrangement of Anode Cover 35)

Figure 1:
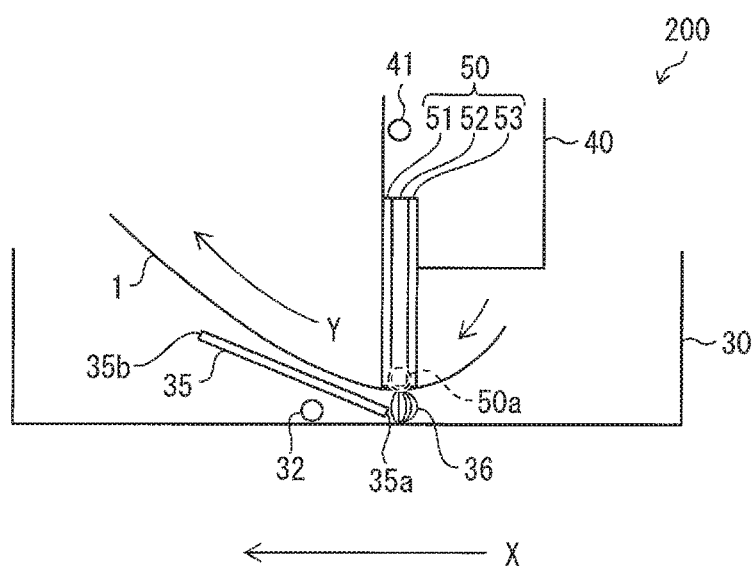
FIG. 1 is a view showing the arrangement of an anode cover in a biomolecule analyzer according to a first embodiment of the present invention.

FIG. 1 is a view showing the arrangement of the anode cover 35 in the biomolecule analyzer 200 according to the present embodiment. This drawing illustrates only a part of the members provided to the biomolecule analyzer 200. In the example of FIG. 1, the anode cover 35 has a flat-plate shape The anode cover 35 has an end 35*a* and end 35*b* that face each other. In the conveying direction X, the end 35*a* is closer than the end 35*b* to the contact location (matching the dispensing part 50*a*) between the transfer membrane 1 and electrophoresis gel chip 50. In other words, in the conveying direction X, the end 35*b* is farther than the end 35*a* from the dispensing part 50*a*.

The anode cover 35 slopes at a certain angle relative to the conveying direction X of the transfer membrane 1. The certain angle referred to herein is an angle at which the end 35*a* is closer to the anode 32 than the end 35*b* (bottom part of anode buffer tank 30) in a direction orthogonal to the in-plane direction of the transfer membrane 1. In other words, it is an angle at which the end 35*b* becomes closer to the anode buffer liquid surface than the end 35*a* in a direction orthogonal to the in-plane direction of the transfer membrane 1.

Since the anode cover 35 slopes as shown in FIG. 1, it is possible to set free bubbles generating at the anode 32 in the lifting direction Y of the transfer membrane 1 along the surface of the anode cover 35. In other words, bubbles escape in a direction distancing from the dispensing part 50, and do not move to the side of the end 35*a* (side of dispensing part 50*a*). As a result thereof, bubbles will not negatively influence the contact location between the transfer membrane 1 and electrophoresis gel chip 50.

(Constricting of Electric Line of Force)

Figure 4:
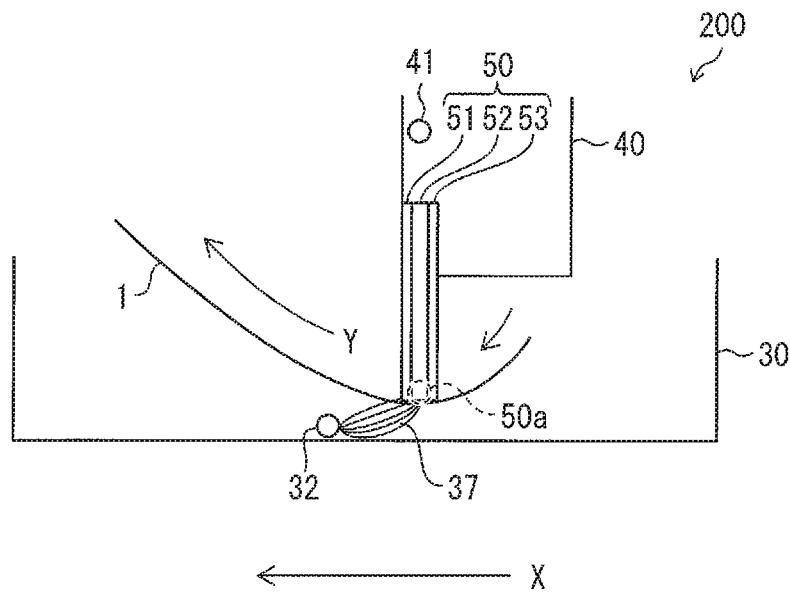
FIG. 4 is a view showing a span of an electric line of force arising in the case of there being no anode cover in the first embodiment of the present invention.

As mentioned above, the anode 32 is not immediately below the dispensing part 50*a*, but is arranged at a position separated a certain distance from the dispensing part 50*a* in the conveying direction X. For this reason, if there is no anode cover 35, the electric line of force 37 arising from the dispensing part 50*a* during electrophoresis will widen greatly as shown in FIG. 4. FIG. 4 is a view showing the span of the electric line of force 37 arising in the case of there being no anode cover 35. As shown in this drawing, when the electric line of force 37 that has greatly widened arises, the analyte dispensed from the dispensing part 50*a* will greatly disperse, a result of which there is a possibility of causing the separability of analyte to greatly decline.

On the other hand, in the present embodiment, as shown in FIG. 1, the end 35*a* of the anode cover 35 is positioned at a lower part of the end on a side of the anode 32 at the contact location between the electrophoresis gel chip 50 and transfer membrane 1. Since the anode cover 35 is constituted from an insulating material, the electric line of force 36 arising from the dispensing part 50*a* is inhibited by the anode cover 35 existing nearest the dispensing part 50*a*, and does not widen towards the anode 32. As a result thereof, as shown in FIG. 1, it is possible to cause the constricted electric line of force 36 to arise from the dispensing part 50*a*. It is thereby possible to greatly improve the separability of analyte.

In addition, the anode cover 35 can be easily detached from the biomolecule analyzer 200. For this reason, it is possible to easily clean or wash the anode cover 35 at fixed intervals. Furthermore, it is also possible to replace the anode cover 35 which has degraded with time with a new article.

Second Embodiment

A second embodiment according to the present invention will be explained hereinafter based on FIG. 5.

Figure 5:
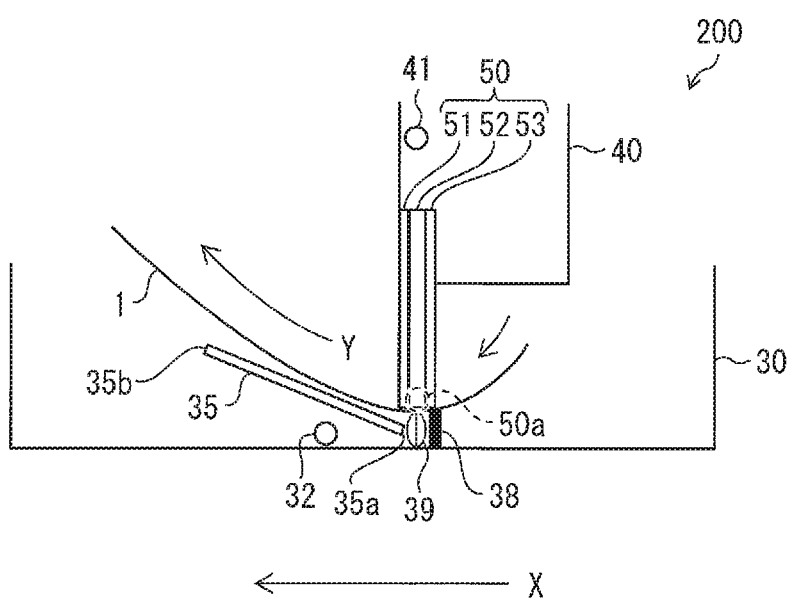
FIG. 5 is a view showing an arrangement of a constricting member and an electric line of force arising from an dispensing part in a second embodiment of the present invention.

FIG. 5 is a view showing the arrangement of a constriction member 38 and an electric line of force 39 arising from the dispensing part 50*a*. As shown in this drawing, the biomolecule analyzer 200 according to the present embodiment further includes the constriction member 38 (second insulating member), in addition to the respective members included by the biomolecule analyzer 200 according to the first embodiment.

The constriction member 38 is configured by an insulating material. In the present embodiment, the material of the constriction member 38 is the same as the material of the anode cover 35; however, it is not necessarily limited thereto.

The constriction member 38 is arranged perpendicular to the transfer membrane 1 at a lower part of an end of the dispensing part 50*a* that is an opposite side to the side of the anode 32. Since the constriction member 38 is insulating, the electric line of force 39 arising from the dispensing part 50*a* is inhibited by the constriction member 38, and cannot spread to an opposite side to the side of the anode 32. As a result thereof, it is possible to further constrict the electric line of force 39 than the electric line of force 36 shown in FIG. 1 occurring in the case of there not being the constriction member 38. It is thereby possible to even more greatly improve the separability of analyte.

Third Embodiment

Figure 6A:
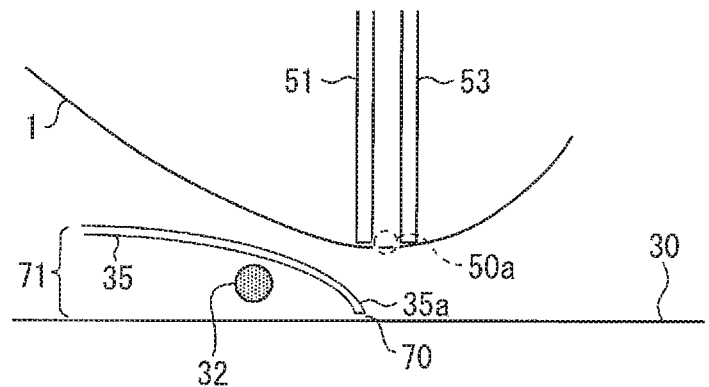
FIG. 6 is a view showing a configuration of an electrode cover in a third embodiment of the present invention.

A third embodiment of the present invention will be explained herein based on FIG. 6.

FIG. 6 is a view showing the configuration of the anode cover 35 in the biomolecule analyzer 200 according to the present embodiment.

The respective members included by the biomolecule analyzer 200 shown in FIG. 6(*a*) or (*b*) are the same as the biomolecule analyzer 200 according to the first embodiment. However, it differs from the first embodiment in the point of a slit 70 (gap) being provided between the anode cover 35 and the bottom face of the anode buffer tank 30.

In FIG. 6(*a*), the slit 70 is provided between the end 35*a* of the anode cover 35 and the bottom face of the anode buffer tank 30. This slit 70 is arranged in a perpendicular direction relative to the conveying direction X, or arranged lower than the anode 32. Furthermore, the slit 70 is arranged immediately below the dispensing part 50*a*.

As shown in FIG. 6(*a*), a side at the end 35*b* of the anode cover 35 is arranged higher than the anode 32. A wide opening part 71 is thereby formed in the anode cover 35 at a side of an end 354*b*. Heat and bubbles generate at the anode 32 during electrophoresis. Convective flow of anode buffer occurs at the periphery of the anode 32 due to this heat. Since the opening part 71 is wider than the slit 70, the anode buffer containing bubbles comes to more easily move to the opening part 71 than the slit 70 due to the convective flow according to heat. As a result thereof, it is possible to further prevent bubbles generating from the anode 32 from heading towards the dispensing part 50*a*.

In FIG. 6(*b*), the anode cover 35 curves at the lower part of the dispensing part 50*a*, and the end 35*a* is arranged at a lower part of the anode 32. Therefore, the slit 70 provided between the end 35*a* and the bottom face of the anode buffer tank 30 is arranged lower than the anode 32. According to this configuration, the electric line of force 72 arising from the dispensing part 50a is inhibited by the anode cover 35, and will not widen towards the anode 32. In other words, the electric line of force 72 is constricted along the anode cover 35 towards the slit 70, which is below the anode 32. It is thereby possible to greatly improve the separability of analyte.

Figure 6B:
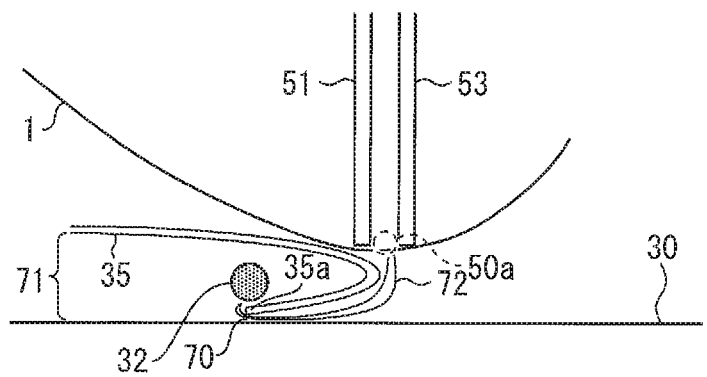

Herein, the wide opening part 71 is formed in the anode cover 35 at the side of the end 35b, also in the configuration shown in FIG. 6(b). Therefore, similarly to the configuration shown in FIG. 6(a), it is possible to further prevent the bubbles generating from the anode 32 from heading towards the dispensing part 50a.

Figure 6C:
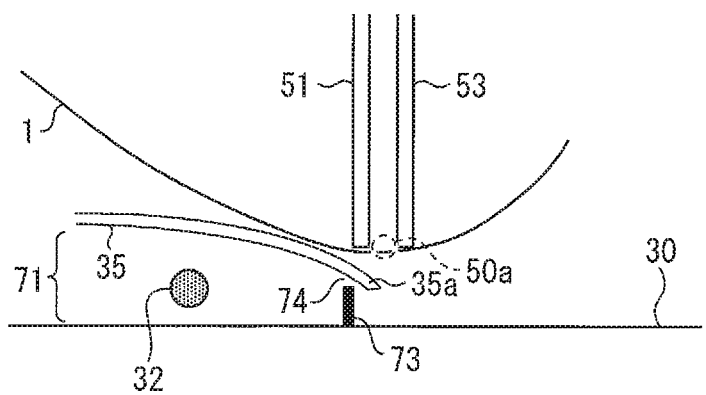

The biomolecule analyzer 200 shown in FIG. 6(c) further includes an insulating upright member 73 (first insulating member) that is long and narrow lengthwise provided to the bottom face of the anode buffer tank 30, in addition to the respective members included by the biomolecule analyzer 200 according to the first embodiment. The upright member 73 is arranged perpendicularly to the transfer membrane 1, at a lower part of an end of the dispensing part 50a on a side of the anode 32. The anode cover 35 is extended so far as the upper part of the upright member 73.

In the configuration shown in FIG. 6(c), the slit 70 is formed between the end 35a of the anode cover 35 and the bottom face of the anode buffer tank 30. In place thereof, the slit 74 is provided between a location slightly more to the end 35b of the anode cover 35 than the end 35a, and the upright member 73. In other words, the slit 74 is provided at a location separated by a certain distance (equal to the height of the upright member 73) from the bottom face of the anode buffer tank 30.

Herein, the wide opening part 71 is formed in the anode cover 35 at a side of the end 35b thereof, also in the configuration shown in FIG. 6(c). Therefore, similarly to the configuration shown in FIG. 6(a), it is possible to further prevent bubbles generating from the anode 32 from heading towards the dispensing part 50a as a result thereof.

Fourth Embodiment

A fourth embodiment according to the present invention will be explained hereinafter based on FIG. 7.

The respective members included by the biomolecule analyzer 200 according to the present embodiment are the same as the biomolecule analyzer 200 according to the first embodiment. However, the sloping direction of the anode cover 35 differs from the first embodiment.

Figure 7A:
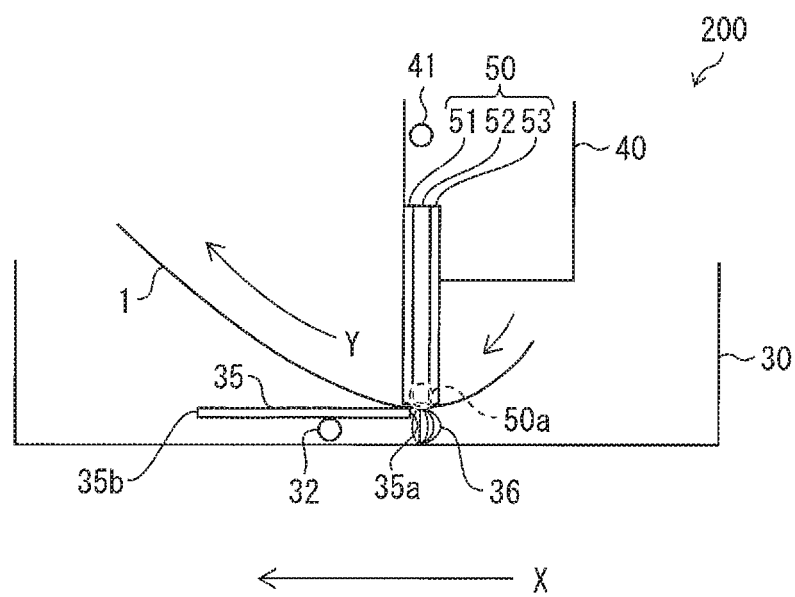
FIG. 7 is a view showing an arrangement of an anode cover in a fourth embodiment of the present invention.

FIG. 7(a) is a view showing the arrangement of the anode cover 35 in the case of viewing the biomolecule analyzer 200 from the left side in the conveying direction X. As shown in this drawing, the anode cover 35 does not slope relative to the conveying direction X.

Figure 7B:
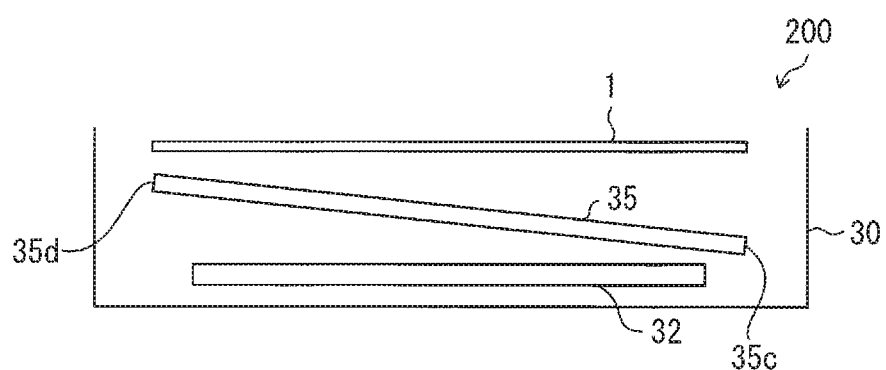

FIG. 7(b) is a view showing the arrangement of the anode cover 35 in the case of viewing the biomolecule analyzer 200 from an end point side in the conveying direction X. As shown in this drawing, the anode cover 35 slopes at a certain angle relative to the direction orthogonal to the conveying direction X and parallel to the in-plane direction of the transfer membrane 1. More specifically, among the pair of ends 35c and 35d possessed by the anode cover 35 in a direction orthogonal to the in-plane direction of the transfer membrane 1, the end 35c positioned at the left side in the conveying direction X is closer to the anode 32 than the end 35d positioned at the right side in the conveying direction X. In other words, in the direction orthogonal to the in-plane direction of the transfer membrane 1, the end 35d is closer to the liquid surface of the anode buffer than the end 35c.

Since the anode cover 35 slopes as shown in FIG. 7(b), it is possible to set free bubbles generating at the anode 32 to a side at the end 35d of the anode cover 35, i.e. in a direction perpendicular to the lifting direction Y of the transfer membrane 1. As a result thereof, the bubbles will not move to the side of the dispensing part 50a; therefore, bubbles will not negatively influence the contact location between the transfer membrane 1 and electrophoresis gel chip 50.

It should be noted that the slope of the anode cover 35 is not limited to that shown in FIG. 7(b). The anode cover 35 may slope at an angle at which the end 35c is closer to the liquid surface of anode buffer than the end 35d. In this case, the bubbles generated at the anode 32 can be set free to the side of the end 35c.

Fifth Embodiment

A fifth embodiment according to the present invention will be explained below based on FIGS. 8 to 11.

(Framed Transfer Membrane 110)

Figure 9A:
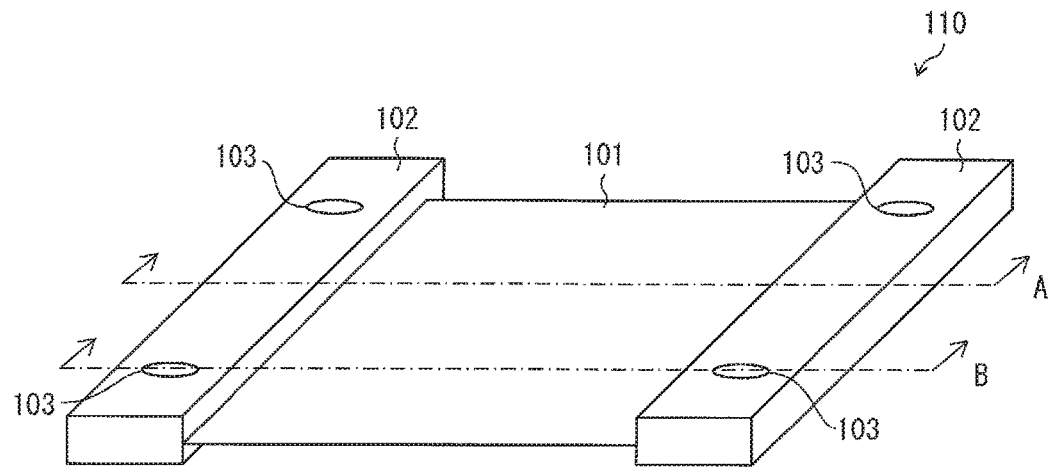
FIG. 9 is a view illustrating an outline of a framed transfer membrane according to the fifth embodiment of the present invention.
Figure 9B:
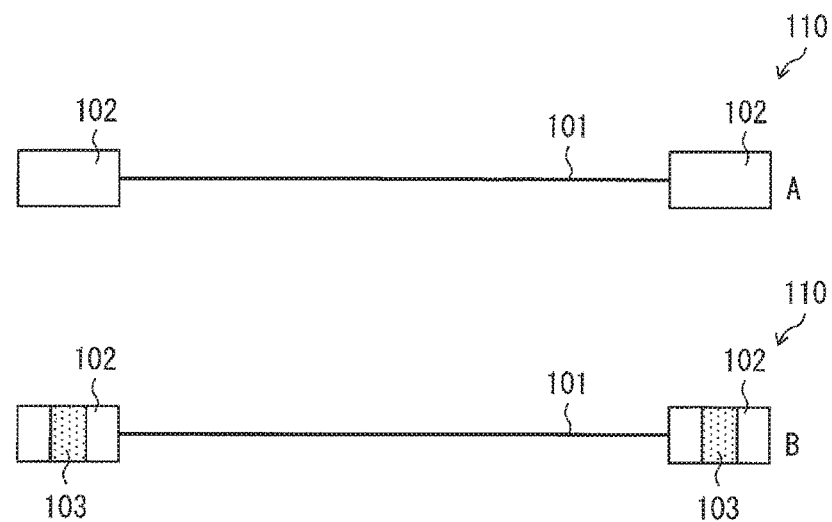

First, the framed transfer membrane used in the biomolecule analyzer according to the present embodiment will be explained hereinafter by referencing FIG. 9. FIG. 9(a) is a view illustrating an outline of the framed transfer membrane 110. FIG. 9(b) provides cross-sectional views along the line A and line B in FIG. 9(a).

As shown in FIG. 9(a), the framed transfer membrane 110 is supported separately by the pair of frames (frame members) 102 at a side of the transfer membrane 101 (first side) and a side facing this side (second side).

As shown in the cross-sectional views along the line A and line B in FIG. 9(b), the framed transfer membrane 110 more preferably is provided with fitting parts (through holes) of open form through which the frame 102 passes, as fitting parts 103 of the pair of frames 102. The fitting parts 103 can respective fit into the fitting parts of a corresponding convex form. It is thereby possible to fix the framed transfer membrane 110 and biomolecule analyzer with the fitting parts 103.

The framed transfer membrane 110 can tighten the transfer membrane 101 without slack by horizontally fixing the pair of frames 102 to separate from each other. In addition, since it is possible to fix the transfer membrane 101 which is sectioned into a predetermined shape in advance by the frame 102, the framed transfer membrane 110 can be installed in the biomolecule analyzer while imparting easy and appropriate tension to the transfer membrane 101. For this reason, it is possible to prevent warping of the blot when fixing to the biomolecule analyzer and transferring analyte by direct blotting.

In addition, with the framed transfer membrane 110, it is possible to use the frame 102 as a sinker of the transfer membrane 101. For this reason, it is possible to prevent the transfer membrane 101 in the reagent from moving inside a reagent tank such as a shaker, and irregularity arising in the antibody response. Furthermore, the framed transfer membrane 110 is a simple configuration consisting of the transfer membrane 101 and pair of frames 102; therefore, compared with one that broadly fixes the transfer membrane smoothly by fixing the entire periphery by a frame, and one that broadly fixes the transfer membrane by a curved frame, it is not bulky and, for example, it is possible to reduce the amount of antibody used when performing Western blotting.

(Transfer Membrane 101)

The transfer membrane 101 is a membrane for adsorbing and retaining biomolecular sample (reagent) separated by the separation unit of the biomolecule analyzer. Herein, it is preferable for the transfer membrane 101 to be able to stably preserve a biomolecular sample (reagent) separated by the separation unit over a long period, and further, and to be an absorbing/retaining body of biomolecular samples that facilitates subsequent analysis. As the material of the transfer membrane 101, it is preferably a material having high strength, and having high sample binding capacity (adsorbable weight per unit volume). As the transfer membrane 101, a polyvinylidene fluoride (PVDF) membrane or the like is suited in the case of the sample being protein. It should be noted that it is preferable to perform hydrophilization treatment using methanol or the like in advance on the PVDF membrane. Otherwise, a membrane conventionally used in the adsorption of proteins, DNA and nucleic acids such as a nitrocellulose membrane or nylon membrane can also be used.

As the biomolecular samples that can be separated and adsorbed in the biomolecule analyzer, although proteins, DNA and RNA can be exemplified, it is not limited thereto. For example, a preparation from biological material (e.g., cell strain, tissue culture, or tissue fragment), a commercially available reagent, and the like are also included among examples of the sample. Furthermore, polypeptides or polynucleotides are also types of samples.

(Frame 102)

For each of the pair of frames 102, the length of the frame 102 is sufficient if longer than the length of one side of the transfer membrane 101 to be fixed. In addition, the frame 102 preferably consists of an insulating material. As the insulating material, it is possible to use a resin such as polymethylmethacrylate (acrylic), polystyrene, polyethylene, polypropylene, polyethylene terephthalate (PET), polyacetal (POM) and polyether ether ketone (PEEK), or glass.

In addition, hydrophilization treatment is more preferably conducted on the surface of the frame 102. For example, a coating layer may be provided to the surface of the frame 102 consisting of the above-mentioned materials. It is thereby possible to prevent a reagent such as protein dispensed from the dispensing part of the separation unit from adhering to the surface of the frame 102, and possible to prevent the frame 102 from being contaminated.

It should be noted that the water contact angle to the surface of the frame 102 is preferably no more than 90°, and more preferably no more than 60°. By establishing the water contact angle to the surface of the frame 102 as no more than 90°, it is possible to suitably prevent the frame 102 from being contaminated by reagent.

(Biomolecule Analyzer 201)

Figure 10:
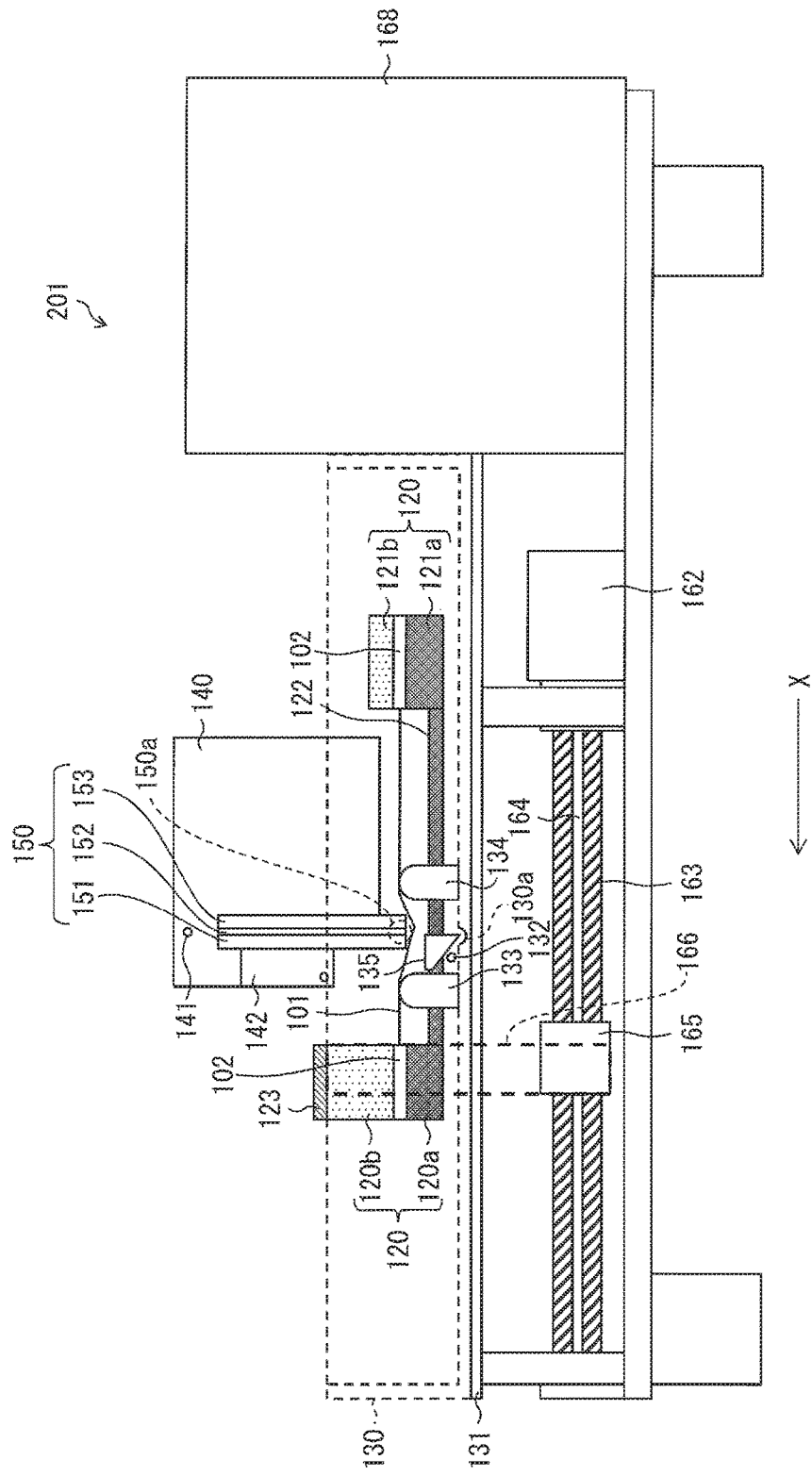
FIG. 10 is a view illustrating an outline of a biomolecule analyzer according to an embodiment of the invention.

Next, a biomolecule analyzer 201 according to an embodiment of the present invention will be explained in detail by referencing FIG. 10. FIG. 10 is a view illustrating an outline of the biomolecule analyzer 200 according to the embodiment of the present invention. As shown in this figure, the biomolecule analyzer 201 includes a clamp 120, an anode buffer tank 130 (buffer tank), an anode stage 131, a cathode buffer tank 140, an electrophoresis gel chip 150 (separation unit) and a conveying part, and a first concave part 130a is provided to the bottom part of the anode buffer tank 130.

In the biomolecule analyzer 201, the anode buffer tank 130 is fixed in a removable state relative to the anode stage 131. The clamp 120 is arranged inside the anode buffer tank 130, and the framed transfer membrane 110 is fixed to the clamp 120 inside of the anode buffer tank 130. The cathode buffer tank 140 is fixed in a removable state relative to the anode buffer tank 130. The electrophoresis gel chip 150 is arranged in the biomolecule analyzer 201 so that, among both end parts opposing each other, one end part is positioned inside of the anode buffer tank 130, and the other end part is positioned inside of the cathode buffer tank 140.

An overview of the biomolecule analyzer 201 is as follows. The electrophoresis gel chip 150 separates the analyte introduced to the separation gel 152 by way of electrophoresis, and dispenses the separated analyte through a dispensing part 150a, which is at one end of the electrophoresis gel chip 150, onto the transfer membrane 101. The conveying part conveys the transfer membrane 101 in a conveying direction X (direction from a side (first side) at which the frame 102 of the framed transfer membrane 110 is provided towards another side (second side) at which the frame 102 is provided). The dispensed analyte is thereby adsorbed at a position according to the timing at which dispensed on the transfer membrane 101 (position opposing the electrophoresis gel chip 150 at the timing dispensed). The separated analyte is thereby transferred to the transfer membrane 101.

(Clamp 120)

As shown in FIG. 10, the clamp 120 includes front clamps 120a and 120b, rear clamps 121a and 121b, and a clamp frame 122. The front clamps 120a and 120b are arranged at a conveying end point side upon the transfer membrane 101 being conveyed, while the rear clamps 121a and 121b are arranged at a conveying starting point side.

In the clamp 120, the front clamp 120a and front clamp 120b are fixed so as to be able to release by a jig. Fitting parts (not illustrated) are provided at two locations on the front clamp 120a, and relative to these fitting parts, the fitting parts 103 provided at two locations on one frame 102 shown in FIG. 9(a) are respectively fitted. Subsequently, one frame 102 is inserted between and fixed by the front clamp 120a and front clamp 120b.

Similarly, in the clamp 120, the rear clamp 121a and rear clamp 121b are fixed so as to be able to release by a jig. Fitting parts (not illustrated) are provided at two locations on the rear clamp 121a, and relative to these fitting parts, the fitting parts 103 provided at two locations on the other frame 102 shown in FIG. 9(a) are respectively fitted. Subsequently, the other frame 102 is inserted between and fixed by the rear clamp 121a and rear clamp 121b.

The clamp frame 122 fixes the front clamp 120a and rear clamp 121a in a state isolating by a certain distance. For this reason, when fixing the framed transfer membrane 110 by way of the clamp 120, the transfer membrane 101 is fixed in a state tightened without slack. Furthermore, the clamp frame 122 fixes the front clamp 120a and rear clamp 121b from a lateral side to the conveying direction of the transfer membrane 101 (outer side of two sides not supported by the frames 102). When fixing the framed transfer membrane 110 to the biomolecule analyzer 201 through the clamp 120, it is thereby possible to arrange the framed transfer membrane 110 so that the clamp frame 122 does not contact the electrophoresis gel chip 150 as well as guides 133 and 134 in the conveying path of the transfer membrane 101.

A carrier 123 is provided to the front clamp 120b. When installing the clamp 120 to an inner side of the anode buffer tank 130, the clamp 120 can be fixed in a removable state to a guide pole 166 arranged at an outer side of the anode buffer tank 130 via the carrier 123.

(Anode Buffer Tank 130)

In FIG. 10, the anode buffer tank (buffer solution tank) 130 is shown with a dotted line. As shown in FIG. 10, the anode buffer tank 130 includes an anode (electrode) 132, guides (support members) 133 and 134, as well as an anode cover 135 (electrode cover). In addition, a concave part 130a is provided to the bottom part of the anode buffer tank 130.

Anode buffer is filled in the anode buffer tank 130. As the anode buffer, for example, it is possible to use buffer solutions such as a Tris/glycine-based buffer solution, acetic acid buffer solution, sodium carbonate-based buffer solution, CPS buffer solution, Tris/boric acid/EDTA buffer solution, Tris/acetic acid/EDTA buffer solution, MOPS, phosphoric acid buffer solution, and Tris/tricine-based buffer solution. The framed transfer membrane 110 fixed to the clamp 120 is established in the anode buffer filled inside of the anode buffer tank 130.

The anode 132 is a long and narrow rod-shaped electrode configured from platinum wire or the like. The anode 132 is provided at the bottom of the anode buffer tank 130 so that the length direction thereof is perpendicular to the conveying direction X of the framed transfer membrane 110. The anode 132 is not immediately below the dispensing part 150a of the electrophoresis gel chip 150, but is rather arranged at a position separated by a certain distance from the dispensing part 150a in the conveying direction X. This position is a position that allows for application of a voltage between the anode 132 and cathode 141, from a back face of the transfer membrane 101 on a side opposing the electrophoresis gel chip 150, when the framed transfer membrane 110 is installed.

The guides 133 and 134 are support members that each support a pair of positions interposing from the front/rear in the conveying direction a position on the transfer membrane 101 at which the electrophoresis gel chip 150 abuts (contacts), from the opposite side to the electrophoresis gel chip 150 of the transfer membrane 101. The guides 133 and 134 are provided at the bottom of the anode buffer tank 130, on the conveying path on which the framed transfer membrane 110 is conveyed. The guides 133 and 134 are arranged so that the height direction of each is parallel to the in-plane direction of the electrophoresis gel chip 150, and the framed transfer membrane 110 perpendicularly intersects the conveying direction X in which the framed transfer membrane 110 is delivered. The guides 133 and 134 thereby support the transfer membrane 101 from the back face of the transfer membrane 101 that is a side opposing the electrophoresis gel chip 150, in parallel to the length direction of an end part of the electrophoresis gel chip 150 on a side of the dispensing part 150a.

(Anode Cover 135)

The anode cover 135 is provided to abut the anode 132 or separate from the anode 132, between the anode 132 and the contact location of the transfer membrane 101 and electrophoresis gel chip 150. Although described later in detail, the biomolecule analyzer 201 can set free bubbles generating from the anode 132 (electrode) to the top part of the anode buffer tank 130 by including the anode cover 135; therefore, it is possible to prevent bubbles from negatively influencing the contact location between the transfer membrane 101 and electrophoresis gel chip 150.

The anode cover 135 is configured from an insulating material. As the insulating material, it is possible to use a resin such as polymethylmethacrylate (acrylic), polystyrene, polyethylene, polypropylene, polyethylene terephthalate (PET), polyacetal (POM) and polyether ether ketone (PEEK), or glass.

In addition, it is more preferable for hydrophilization treatment to be conducted on the surface of the anode cover 135. For example, a coating layer may be provided to the surface of the frame 102 consisting of the above-mentioned material. It is thereby possible to facilitate setting free the bubbles generating from the anode 132 from the top part of the anode buffer tank 130 along the surface of the anode cover 135.

It should be noted that the water contact angle of the surface of the anode cover 135 is preferably no more than 90° C., and more preferably no more than 60°. By establishing the water contact angle of the surface of the anode cover 135 as no more than 90°, it is possible to further facilitate setting free bubbles along the surface of the anode cover 135.

(Cathode Buffer Tank 140)

As shown in FIG. 10, the cathode buffer tank 140 includes a cathode 141 and a lock 142. The cathode 141 is a long and narrow rod-shaped electrode configured from platinum wire or the like. The cathode 141 is arranged at a top part on the inner side of the cathode buffer tank 40 (immediately above the separation gel 152) so that the length direction thereof is orthogonal to the conveying direction of the transfer membrane 101. In other words, the length direction of the cathode 141 is parallel to the length direction of the anode 132.

The cathode buffer is filled into the cathode buffer tank 140. It is possible to use a similar buffer solution to the anode buffer solution as the cathode buffer.

The electrophoresis gel chip 150 is fixed inside of the cathode buffer tank 140 by the lock 142. At this time, the end part of the electrophoresis gel chip 150 on the opposite side to the dispensing part 150a is immersed in the cathode buffer filled in the cathode buffer tank 140. On the other hand, the end part of the electrophoresis gel chip 150 on the side of the dispensing part 150a is immersed in the anode buffer filled in the anode buffer tank 130.

As shown in FIG. 10, the end part of the separation gel 152 on the opposite side to the side of the dispensing part 150a is facing the cathode 141. On the other hand, the end part of the separation gel 152 on the side of the dispensing part 150a is not facing the anode 132. In this way, the end part of the separation gel 152 on the side of the dispensing part 150a is separated by a fixed distance from the anode 132 in the conveying direction of the transfer membrane 101.

(Electrophoresis Gel Chip 150)

As shown in FIG. 10, the electrophoresis gel chip 150 includes an insulating plate 151, separation gel 152 and insulating plate 153. The insulating plate 151 and insulating plate 153, for example, are formed by plates consisting of insulators such as glass and acrylic. The separation gel 152 is formed between the insulating plate 151 and insulating plate 153.

The separation gel 152 is a gel for separating the introduced biomolecule sample (analyte) according to molecular weight. As examples of the separation gel 152, polyacrylamide gel, agarose gel and the like are exemplified, and it is preferable to use a gel made by combining with a buffer solution in the aforementioned suitable compositions. The separation gel 152 can form by filling into the electrophoresis gel chip 150 prior to installing the electrophoresis gel chip 150 to the cathode buffer tank 140.

The electrophoresis gel chip 150 is arranged in the biomolecule analyzer 201 so as to perpendicularly abut against the transfer membrane 101. Furthermore, the electrophoresis gel chip 150 is arranged vertically. The dispensing part 150a of the electrophoresis gel chip 150 contacts the surface of the transfer membrane 101. The biomolecule sample is supplied to the separation gel 152 through the end of the electrophoresis gel chip 150 that is facing the dispensing part 150a and is arranged inside the cathode buffer tank 140. After the biomolecule sample is supplied, electrophoresis is performed by applying a voltage between the anode 132 and cathode 141. As a result thereof, the analyte is transferred to the transfer membrane 101 through the dispensing part 150a.

(Conveying Part)

As shown in FIG. 10, the conveying part includes a motor 162, ball screw 163, guide shaft 164, shaft holder 165, and guide pole 166.

With the conveying part, it is possible to move the shaft holder 165 in the conveying direction X along the guide shaft 164, by causing the ball screw 163 to rotate with the motor 162. The guide pole 166 is fixed to the shaft holder 165, and the guide pole 166 supports the carrier 123 provided to the clamp 120 from outside of the anode buffer tank 130.

The conveying part causes the framed transfer membrane 110 arranged inside of the anode buffer tank 130 to move in the conveying direction via the guide pole 166 arranged outside of the anode buffer tank 130, by causing the motor 162 to rotate according to the above-mentioned configuration.

(Operation of Biomolecule Analyzer 201)

Operation of the biomolecule analyzer 201 will be explained below. First, the framed transfer membrane 110 is fixed by the clamp 120, and arranged at the inner side of the anode buffer tank 130 filled with the anode buffer. The transfer membrane 101 of the framed transfer membrane 110 is fixed in a state supported from the lower side by the guide 133 and guide 134.

Subsequently, the cathode buffer tank 140 to which the electrophoresis gel chip 150 is fixed by the lock 142 is fixed to the top of the anode buffer tank 130. At this time, the cathode buffer tank 140 is installed in a state such that pushes the electrophoresis gel chip 150 to the above the transfer membrane 101. The transfer membrane 101 is thereby fixed in a state folded back (valley fold shape) so as to be convex to an opposite side to the electrophoresis gel chip 150 by touching the guide 133, guide 134 and electrophoresis gel chip 150.

Next, by applying a voltage between the anode 132 and cathode 141, the transfer membrane 101 of the framed transfer membrane 110 is conveyed in the transfer direction X shown in FIG. 10, in the state as is transferring the analyte dispensed by the electrophoresis gel chip 150 and pushing against the dispensing part of the electrophoresis gel chip 150, in the anode buffer. For this reason, the tension occurring when the transfer membrane 101 is conveyed is focused on the dispensing part provided at the end of the electrophoresis gel chip 150. In other words, the transfer membrane 101 is conveyed in the transfer direction X while pushing against the dispensing part of the electrophoresis gel chip 150 with a constant force.

For this reason, when conveying the transfer membrane 101 with the framed transfer membrane 110, it is possible to prevent a gap from forming between the transfer membrane 101 and the dispensing part of the analyte of the electrophoresis gel chip 150. Therefore, it is possible to suppress dispersing in the anode buffer prior to the analyte dispensed from the dispensing part of the electrophoresis gel chip 150 being transferred to the transfer membrane 101. It is thereby possible to reduce the fluctuation in the band of analyte transferred to the transfer membrane 101, and it is possible to improve the sensitivity of the biomolecule analyzer.

(Arrangement of Anode Cover 135)

Figure 8:
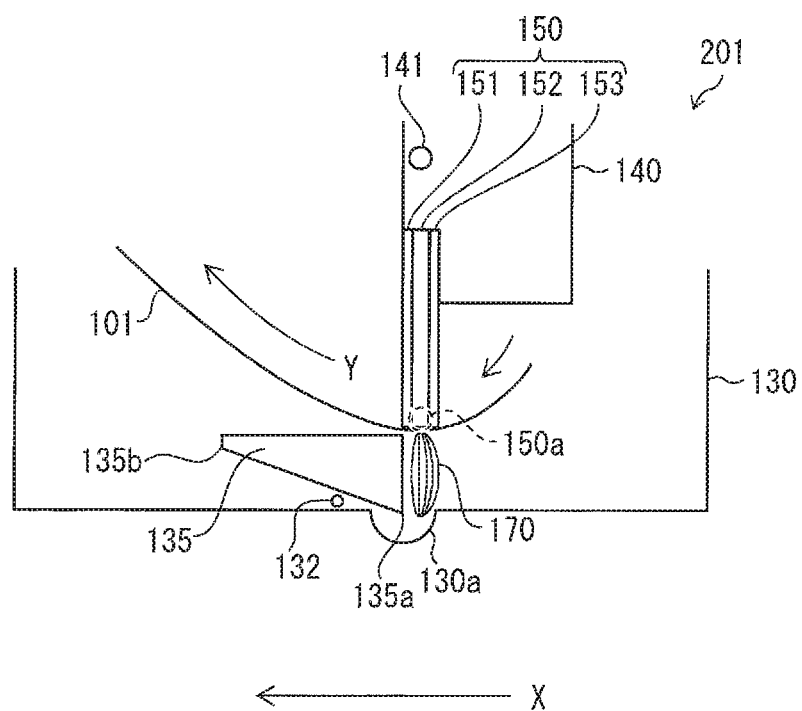
FIG. 8 is a view showing an arrangement of an anode cover of a biomolecule analyzer according to a fifth embodiment of the present invention.

FIG. 8 is a view showing the arrangement of the anode cover 135 in the biomolecule analyzer 201 according to the present embodiment. This drawing illustrates only a part of the members provided to the biomolecule analyzer 201. In the example of FIG. 8, the anode cover 135 is made in a trapezoid having a bottom face that slopes in the conveying direction of the transfer member 101.

The anode cover 135 has, in the bottom face thereof, an end (end part) 135a and end 135b that are orthogonal to the conveying direction X and face each other. In the conveying direction X, the end 135a is closer than the end 135b to the contact location (matching the dispensing part 150a) between the transfer membrane 101 and electrophoresis gel chip 150. In other words, in the conveying direction X, the end 135b is farther than the end 135a from the dispensing part 150a.

The bottom face of the anode cover 135 slopes so that the end 135a is closer to the bottom of the anode buffer tank 130 than the end 135b. In other words, the bottom face of the anode cover 135 slopes so that the end 135b is closer to the liquid surface of the anode buffer than the end 135a. The sloping angle is not particularly limited, and may be a fixed angle, or the sloping angle may vary according to position.

In addition, at the lower part of the contact location between the transfer membrane 101 and the electrophoresis gel chip 150, a first concave part 130a of groove shape is provided in the anode buffer tank 130 so that the longitudinal direction thereof is orthogonal to the conveying direction of the transfer membrane 101. The first concave part 130a has a depth on the order of 2 to 3 mm deep.

The end 135a of the anode cover 135 hangs down towards the first concave part 130a. Preferably, the end 135a of the anode cover 135 is movably inserted in the first concave part 130a by making to follow the longitudinal direction of the first concave part 130a. A bottleneck is thereby formed between the anode cover 135 and first concave part 130a, while arranging the end 135a of the anode cover 135 at a position lower than the bottom face of the anode buffer tank 130 in which the anode 132 is arranged.

Since the anode cover 135 slopes as shown in FIG. 8, it is possible to set free bubbles generating at the anode 132 in the lifting direction Y of the transfer membrane 101 along the surface of the anode cover 135. In addition, since the end 135a of the anode cover 135 is arranged at a position lower than the bottom part of the anode 132, bubbles generating from the anode 132 will not pass through the bottleneck formed by the end 135a and first concave part 130a. For this reason, bubbles escape in the direction distancing from the dispensing part 150a, and will not migrate to the side of the end 135a (side of dispensing part 150a). As a result thereof, bubbles will not negatively influence the contact location between the transfer membrane 101 and electrophoresis gel chip 150.

(Constricting of Electric Line of Force)

As mentioned above, the anode 132 is not immediately below the dispensing part 150a, but is arranged at a position separated a certain distance from the dispensing part 150a in the conveying direction X. For this reason, if there is no anode cover 135, the electric line of force arising from the dispensing part 150a during electrophoresis will widen greatly. If the electric line of force greatly spreads, analyte dispensed from the dispensing part 150a will greatly scatter, a result of which there is a possibility of causing the separability of analyte to greatly decline.

On the other hand, in the present embodiment, the end 135a of the anode cover 135 is arranged above the first concave part 130a provided in the bottom part of the anode buffer tank 130 so as to be positioned at a lower part of an end on the anode 132 side of the contact location between the electrophoresis gel chip 150 and transfer membrane 101, as shown in FIG. 8. Since the anode cover 135 is constituted from an insulating material, the electric line of force 170 arising from the dispensing part 150a is inhibited by the anode cover 135 existing nearest the dispensing part 150a, and does not widen towards the anode 132. In addition, the bottleneck formed by the end 135a of the anode cover 135 and the first concave part 130a of the anode buffer tank 130 is in communication between the anode 132 and dispensing part 150a, and is open towards the dispensing part 150a at the bottom part of the anode buffer tank 130. As a result thereof, as shown in FIG. 8, it is possible to cause the constricted electric line of force 170 to arise from the dispensing part 150a. It is thereby possible to greatly improve the separability of analyte.

In addition, the anode cover 135 can be easily detached from the biomolecule analyzer 201. For this reason, it is possible to easily clean or wash the anode cover 135 at fixed intervals. Furthermore, it is also possible to replace the anode cover 135 which has degraded with time with a new article.

Modified Example

Figure 11A:
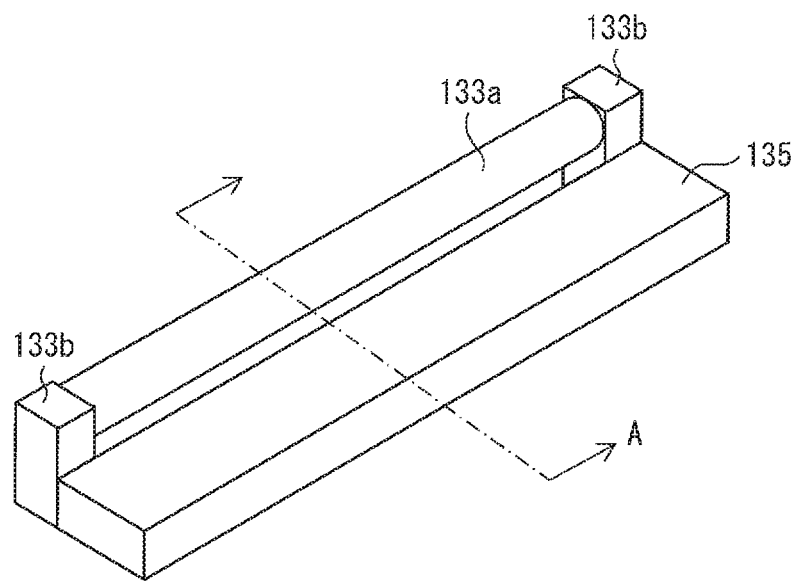
FIG. 11 is a view illustrating an outline of an electrode cover with a support member according to a modified example of the present invention.

The anode cover included by the biomolecule analyzer according to the present embodiment is not limited to the above-mentioned embodiments. For example, as shown in FIGS. 11(a) and (b), the anode cover 135 and guide 133 may be formed integrally. FIG. 11(a) is a view illustrating an outline of the anode cover with a support member according to one modified example of the present invention, and FIG. 11(b) is a cross-sectional view along the line A in FIG. 11(a).

As shown in FIG. 11(a), two support parts 133b of the guide 133 are fixed at both ends on lateral faces in the longitudinal direction of the anode cover 135, and a shaft 133a is supported by these two support parts 133b.

Figure 11B:
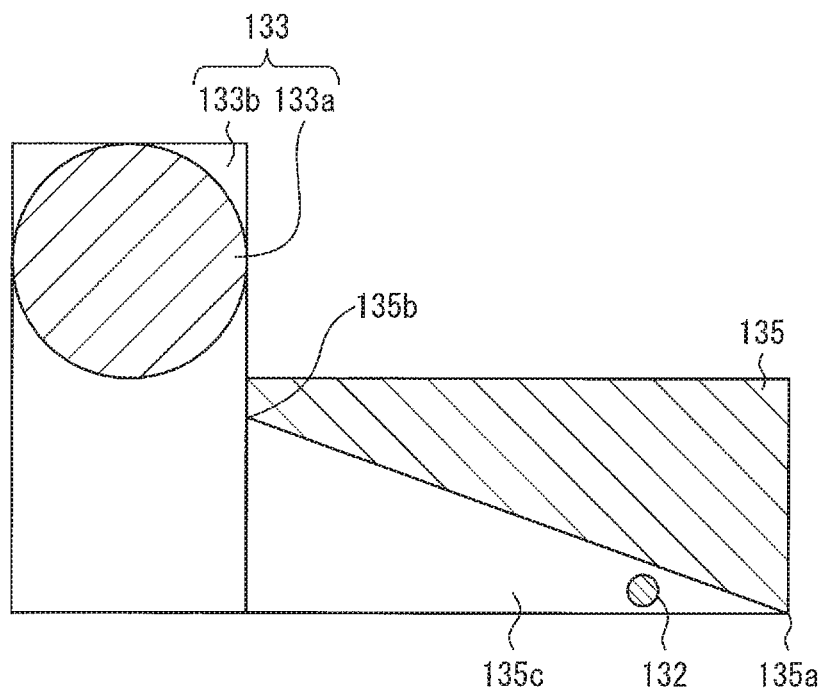

As shown in FIG. 11(b), with the anode cover 135, the support part 133b is fixed on a lateral face on a side of the end 135b, and is open without cover at a lower part of the shaft 133a supported by the support part 133b. In addition, a side wall 135c perpendicular relative to the bottom face of the anode cover 135 is provided along two sides intersecting the end 135a and end 135b at both ends in the longitudinal direction of the anode cover 135 (side wall 135c as seen from behind is shown in FIG. 11(b)).

With the biomolecule analyzer 201, the guide 133 is arranged so as to support the transfer membrane 101 conveyed in the conveying direction by the shaft 133a, and the anode cover 135 has an end 135a arranged on a concave part 130a of the anode buffer tank 130, and the end 135b is arranged at a position farther than the end 135a relative to the contact location between the transfer membrane 101 and electrophoresis gel chip 150. In addition, the side wall 135c of the anode cover 135 is arranged along the conveying direction of the transfer membrane 101.

The bubbles generating from the anode 132 are prevented, by the side wall 135c of the anode cover 135, from flowing towards the contact location between the transfer membrane 101 and electrophoresis gel chip 150, from the two sides along the conveying direction of the anode cover 135. Therefore, the bubbles generating from the anode 132 move from the side of the end 135a of the anode cover 135 along the bottom face of the anode cover 135 and side wall 135c towards the side of the end 135b, and are set free from the bottom part of the shaft 133a of the guide 133 towards the upper part of the anode buffer tank 130. The end 135b of the anode cover 135 is arranged at a position far from the contact location between the transfer membrane 101 and electrophoresis gel chip 150; therefore, bubbles set free from the lower part of the shaft 133a of the guide 133 will not reach the contact location.

Sixth Embodiment

A sixth embodiment according to the present invention will be explained hereinafter based on FIG. 12.

Figure 12A:
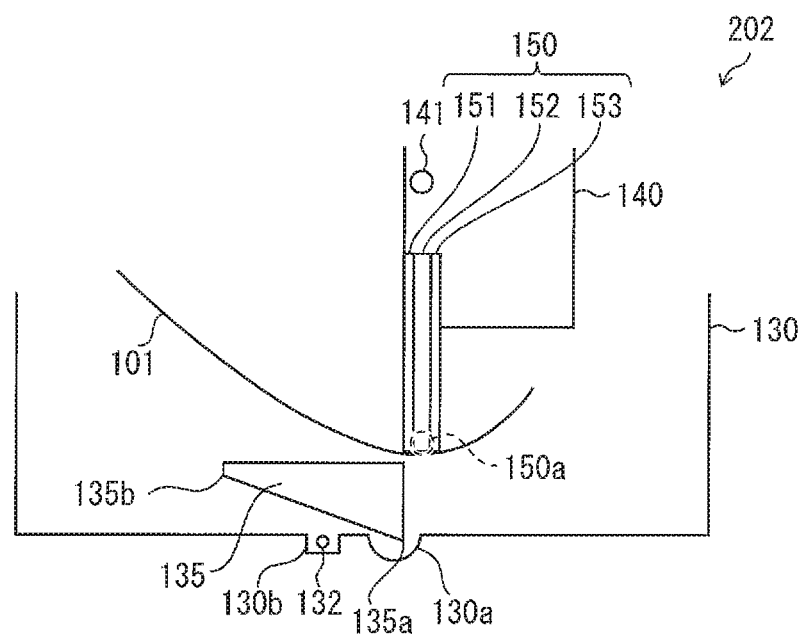
FIG. 12 is a view illustrating an outline of a biomolecule analyzer according to a sixth embodiment of the present invention.

As shown in FIG. 12(a), the respective members of the biomolecule analyzer 202 are the same as the biomolecule analyzer 201 according to the fifth embodiment. However, it differs from the fifth embodiment in the point of, in a anode buffer tank 130, a second concave part 130b being provided at a position separated by a certain distance in the conveying direction from the concave part 130a, and an anode 132 being arranged at an inner side of the second concave part 130b.

The second concave part 130b is provided at a position separated in the conveying direction from the first concave part 130a to the same extent as the position at which the anode 132 is arranged in the fifth embodiment.

Figure 12B:
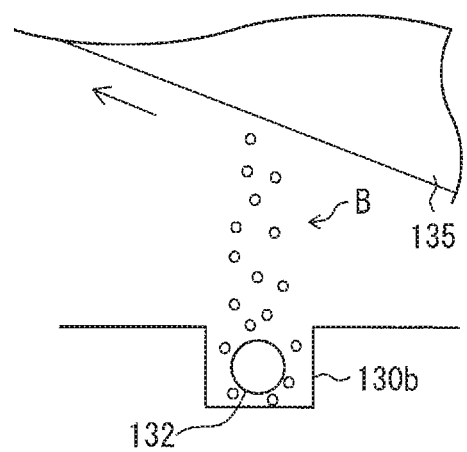

As shown in FIG. 12(b), it is possible to prevent microscopic bubbles B generating from the anode 132 from spreading and moving in a horizontal direction of the anode 132 during electrophoresis, by arranging the anode 132 at an inner side of the second concave part 130b. In addition, microscopic bubbles B generating from the anode 132 can be made to agglomerate at the inner side of the second concave part 130b, and grow into larger bubbles B. It is thereby possible to cause the bubbles B to more suitably rise towards the top part of the second concave part 130b, and possible to make move along the bottom face of the anode cover 135. It is thereby possible to further prevent the microscopic bubbles B generating from the anode 132 from moving towards the dispensing part 150a. Therefore, the bubbles B will not negatively influence the contact location between the transfer membrane 101 and electrophoresis gel chip 150.

It should be noted that the depth of the second concave part 130b may be a depth of an extent capable of accommodating the anode 132 at an inner side; however, it is preferably deeper than the height of the anode 132 in order to allow bubbles to agglomerate more suitably.

Seventh Embodiment

A seventh embodiment according to the present invention will be explained hereinafter based on FIG. 13.

FIG. 13 is a view showing the configurations of the respective anode covers and anode buffer tanks of biomolecule analyzers 203 and 204 according to the present embodiment.

Figure 13A:
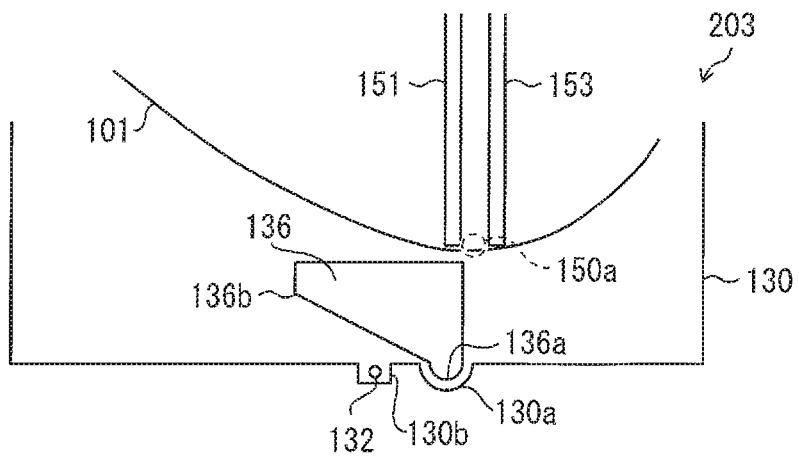
FIG. 13 is a view illustrating outlines of biomolecule analyzers according to a seventh embodiment and eighth embodiment of the present invention.

The biomolecule analyzer 203 shown in FIG. 13(a) includes an anode cover 136 in place of the anode cover 135. Differing from the bottom face of the anode cover 135, a convex part 136a that hangs down towards the first concave part 130a is provided along an end on a side of the dispensing part 150a at the bottom face of the anode cover 136. The longitudinal direction of the convex part 136a is parallel to the longitudinal direction of the first concave part 130a. In the conveying direction of the transfer membrane 101, the convex part 136a is arranged at a position closer to the dispensing part 150a than the anode 132, which is arranged at the inner side of the second concave part 130b.

The convex part 136a is movably inserted in the first concave part 130a, and the anode cover 136 and first concave part 130a thereby form a bottleneck at the bottom face of the anode buffer tank 130.

With the anode cover 136, since the convex part 136a protrudes towards the inner side of the first concave part, it is possible to movably insert the convex part 136a deeply to the inner side of the first concave part 130a. For this reason, when bubbles generating from the anode 132 rise towards the bottom face of the anode cover 136, it is possible to prevent these bubbles from moving towards the side of the dispensing part 150a, and it is possible to make these bubbles move towards the side of the end 136b along the bottom face of the anode cover 136. Therefore, it is possible to further prevent bubbles from negatively influencing the contact location between the transfer membrane 101 and electrophoresis gel chip 150.

In addition, the bottleneck formed by the convex part 136a and first concave part 130a is opened at the lower part of the contact location between the transfer membrane 101 and electrophoresis gel chip 150. For this reason, it is possible to cause a constricted electric line of force to generate from the dispensing part 150a.

Figure 13B:
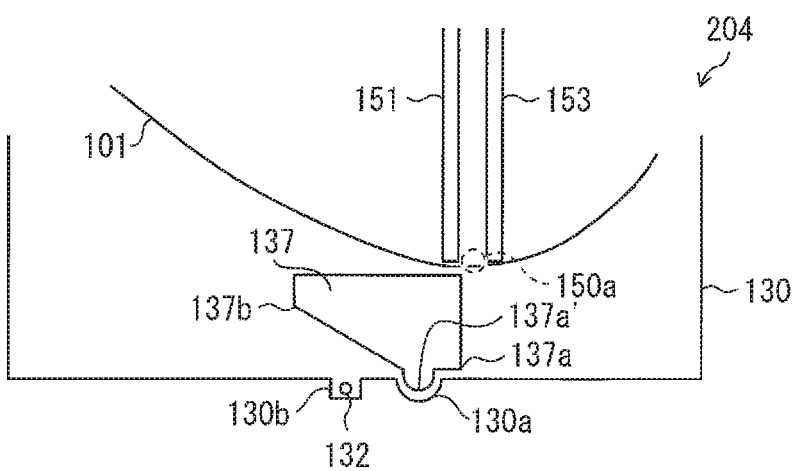

The biomolecule analyzer 204 shown in FIG. 13(b) includes an anode cover 137 in place of the anode cover 135. Differing from the bottom face of the anode cover 135, a convex part 137a' is provided at the bottom face of the anode cover 137 at a position that is farther than the side 137a relative to the dispensing part 150a, and closer than the anode 132 relative to the dispensing part 150a, in the conveying direction of the transfer membrane 101. The convex part 137a' is movably inserted in the first concave part 130a provided at a position opposing the convex part 137a' on the anode buffer tank 130. A bottleneck is thereby formed by the site on the bottom face of the anode cover 137 from the convex part 137a' to the end 137a, and a part of the bottom face of the anode buffer tank 130 including the first concave part 130a. For this reason, it is possible to prevent the bubbles generating from the anode 132 from moving to the side of the dispensing part 150a, by the convex part 137a' provided at a position farther than the side 137a relative to the dispensing part 150a.

In addition, the bottleneck is opened at the bottom part of the dispensing part 150a according to the site from the convex part 137a' to the end 137a, and a part of the bottom face of the anode buffer tank 130 including the first concave part 130a. For this reason, it is possible to cause a constricted electric line of force to arise from the dispensing part 150a.

Eighth Embodiment

An eighth embodiment according to the present invention will be explained hereinafter based on FIG. 14.

Figure 14A:
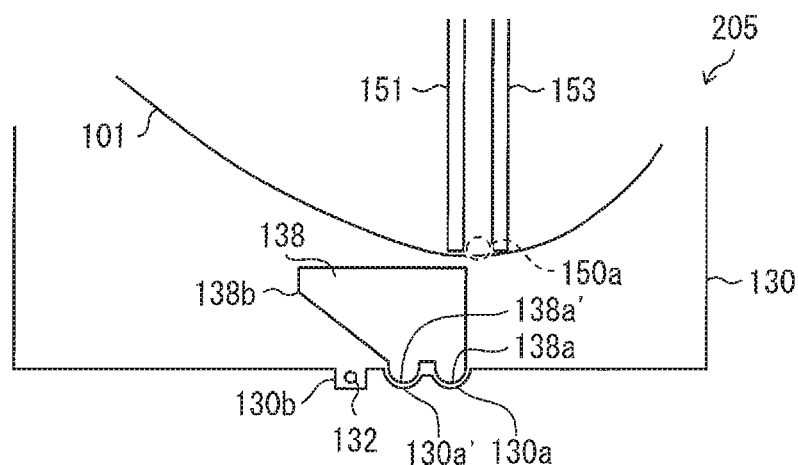
FIG. 14 is a view illustrating an outline of a biomolecule analyzer according to a ninth embodiment of the present invention.

FIG. 14(a) is a view showing the respective configurations of the anode cover and anode buffer tank of the biomolecule analyzer 205 according to the present embodiment.

The biomolecule analyzer 205 shown in FIG. 14(a) includes an anode cover 138 in place of the anode cover 136. In addition, a first concave part consisting of concave parts 130a and 130a' is provided at the bottom part of the anode buffer tank 130. The concave part 130a is provided at the bottom part of the dispensing part 150a in the bottom part of the anode buffer tank 130, and 130a' is provided between the concave part 130a and second concave part 130b. The concave parts 130a and 130a' are provided in parallel to each other so that a longitudinal direction intersects the conveying direction of the transfer membrane 101.

In place of the convex part 136a of the anode cover 136, a plurality of convex parts 138a and 138a' are provided in parallel to the longitudinal direction of the concave parts 130a and 130a' at the bottom face of the anode cover 138. The convex part 138a of the anode cover 138 is movably inserted in the concave part 130a, and the convex part 138a' is movably inserted in the concave part 130a'. A bottleneck is thereby formed by the convex parts 138a and 138a' of the anode cover 138, and the concave parts 130a and 130a' of the anode buffer tank 130.

Figure 14B:
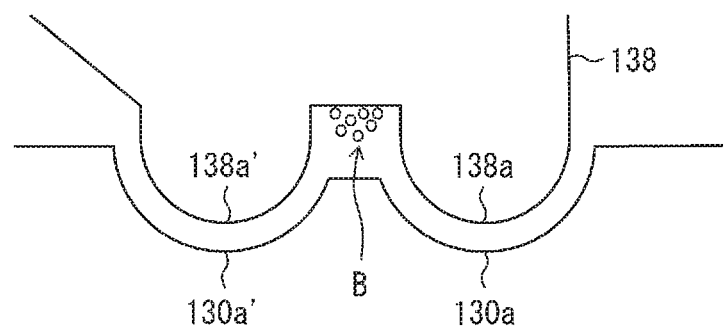

As shown in FIG. 14(b), with the anode cover 138, it is possible to movably insert the convex parts 138a and 138a' deeply towards the inner side of the concave parts 130a and 130a' separately. For this reason, even if the bubbles B generated from the anode 132 move towards the side of the dispensing part 150a past the convex part 138a', it is possible to allow the bubbles B passing the convex part 138a' to temporarily rise inside of the bottleneck, then accumulate between the convex part 138a and the convex part 138a' to separate from the flow of phoresis buffer liquid. It is thereby possible to make the bubbles B hardly flow to the side of the dispensing part 150a due to the flow of phoresis buffer solution. Therefore, it is possible to further prevent the bubbles B generating from the anode 132 from moving towards the side of the dispensing part 150a.

In addition, since the bottleneck formed by the convex parts 138a and 138a' of the anode cover 138, and the first concave parts 130a and 130a' of the anode buffer tank 130 is open at a lower part of the dispensing part 150a, it is possible to cause a constricted electric line of force to arise from the dispensing part 150a.

Other Embodiments

It should be noted that the biomolecule analyzer according to the present invention is not limited to the above-mentioned embodiments. For example, in the biomolecule analyzer according to another embodiment, the shape of the first concave part in a lateral view may be semicircular, or may be a rectangle, V-shape (taper) or the like. In addition, in the case of the electrode cover drooping the concave part hanging down towards the first concave part, the shape in the lateral view of this convex part may also be semicircular, or may be a rectangle, V-shape (taper) or the like. The shapes of the electrode cover and first concave part are not limited so long as able to form a bottleneck in communication with the contact location between the separation unit and transfer membrane, between the electrode cover and first concave part.

In addition, in a biomolecule analyzer according to yet another embodiment, an end side (end) of the electrode cover arranged at the side of the first concave part of the buffer solution tank is arranged at the same height as the bottom face of the buffer solution tank on the first concave part. If the above-mentioned configuration, it is possible to form a bottleneck by the electrode cover and first concave part, while preventing bubbles generating from the electrode from passing over the first concave part and flowing until the contact location between the transfer membrane and electrophoresis gel chip.

In addition, with the biomolecule analyzer according to yet another embodiment, the frame 102 may not be provided to the transfer membrane 101, and the clamp 120 may serve so as to fix the transfer membrane 101 directly.

Supplement

A biomolecule analyzer according to a first aspect of the present invention includes:

a transfer membrane;

a conveying unit that conveys the transfer membrane along a predetermined conveying direction;

a separation unit that perpendicularly abuts the transfer membrane and is installed vertically, separates analyte by way of electrophoresis, and dispenses the analyte that has been separated to the transfer membrane;

an electrode that is disposed at a position separated by a certain distance in the conveying direction from a contact location between the separation unit and the transfer membrane; and an insulating electrode cover that is disposed at an upper part of the electrode to abut the electrode or be separated from the electrode.

According to the above-mentioned configuration, bubbles generating from the anode during electrophoresis are prevented by the anode cover from migrating towards the contact location between the separation unit and transfer membrane. The bubbles generating from the electrode will thereby not negatively influence the contact location between the transfer membrane and separation unit.

According to a second aspect of the present invention, in the biomolecule analyzer of the above-mentioned first aspect, one end part of the electrode cover is at a lower part of an end part of the contact location on a side of the electrode.

According to the above-mentioned configuration, the electric line of force arising from the contact location of the separation unit during electrophoresis is prevented from spreading at the electrode side. As a result thereof, the separability of analyte can be improved.

According to a third aspect of the present invention, the biomolecule analyzer of the above-mentioned second aspect further includes:

a buffer tank in which the electrode is disposed, in which a slit is formed between the one end part of the electrode cover and a bottom face of the buffer tank.

According to the above-mentioned configuration, it is possible to further prevent bubbles generating from the electrode during electrophoresis from migrating towards the slit side (i.e. side of the contact location between the separation unit and transfer membrane).

According to a fourth aspect of the present invention, the biomolecule analyzer of the above-mentioned first aspect further includes:

a buffer tank in which the electrode is disposed, in which the electrode cover is curved to a side of the electrode at a lower part of an end part of the contact location on a side of the electrode, so that one end part of the electrode cover is positioned at a lower part of the electrode, and in which a slit is formed between the one end part of the electrode cover and a bottom face of the buffer tank.

According to the above-mentioned configuration, it is possible greatly improve the separability of analyte, as well as further prevent bubbles generating from the electrode during electrophoresis from migrating towards the slit side (i.e. side of the contact location between the separation unit and transfer membrane).

According to a fifth aspect of the present invention, the biomolecule analyzer of the above-mentioned first aspect further includes:

a first insulating member that is disposed perpendicularly relative to the transfer membrane at a lower part of an end part of the contact location on a side of the electrode side, in which the electrode cover is extended until an upper part of the first insulating member, and in which a slit is formed between the electrode cover and the first insulating member.

According to the above-mentioned configuration, it is possible to further prevent bubbles generating from the electrode during electrophoresis from migrating towards the slit side (i.e. side of the contact location between the separation unit and transfer membrane).

According to a sixth aspect of the present invention, the biomolecule analyzer of any of the above-mentioned first to fifth aspects further includes:

at a lower part of an end part of the contact location on an opposite side to the side of the electrode, an insulating member that is disposed perpendicularly relative to the transfer membrane.

According to the above-mentioned configuration, the electric line of force arising from the contact location of the separation unit during electrophoresis is prevented from spreading to the opposite side to the electrode. As a result thereof, the separability of analyte can be improved.

According to a seventh aspect of the present invention, in the biomolecule analyzer of any of the above-mentioned first to sixth aspects, the electrode cover slopes relative to the conveying direction, and an end part of the electrode cover that is farther from the contact location is farther from the electrode in a direction orthogonal to an in-plane direction of the transfer membrane, than an end part of the electrode cover that is closer to the contact location.

According to the above-mentioned configuration, it is possible to set free bubbles generating from the electrode in a direct distancing from the contact location.

According to an eighth aspect of the present invention, in the biomolecule analyzer of any of the above-mentioned first to sixth aspects, the electrode cover slopes relative to a direction that is orthogonal to the conveying direction and parallel to an in-plane direction of the transfer membrane.

According to the above-mentioned configuration, it is possible to set free bubbles generating from the electrode in a direction distancing from the contact location.

According to a ninth aspect of the present invention, in the biomolecule analyzer of any of the above-mentioned first to eighth aspects, a water contact angle to a surface of the electrode cover is no more than 90°.

According to the above-mentioned configuration, it is possible to further facilitate setting free bubbles generating from the electrode along the surface of the electrode cover.

A biomolecule analyzer according to a tenth aspect of the present invention includes:

a buffer solution tank;

a transfer membrane that is disposed inside the buffer solution tank;

a conveying unit that conveys the transfer membrane along a predetermined conveying direction;

a separation unit that perpendicularly abuts the transfer membrane and is installed vertically, separates analyte by way of electrophoresis, and dispenses the analyte that has been separated to the transfer membrane;

an electrode that is disposed at a position separated by a certain distance in the conveying direction from a contact location between the separation unit and the transfer membrane; and an insulating electrode cover that is disposed between the electrode and the contact location, in which a first concave part is provided at a position on a bottom part of the buffer solution tank that is interposed by the electrode and the contact location, and in which the electrode cover hangs down towards the first concave part.

According to the above-mentioned configuration, it is possible to prevent, by way of the electrode cover, bubbles generating from the electrode from migrating towards the contact location between the separation unit and transfer membrane. In addition, since the electrode cover hangs down towards the first concave part provided in the bottom part of the buffer solution tank, it is possible to prevent bubbles generating form the electrode from passing the first concave part and migrating towards the contact location between the separation unit and transfer membrane. The bubbles generating from the electrode will thereby not negatively influence the contact location between the transfer membrane and separation unit.

In addition, the side of the contact location between the separation unit and transfer membrane and the side of the electrode are in communication by the bottleneck formed by the insulating electrode cover and the first concave part; therefore, it is possible to constrict the electric line of force from the contact location towards the bottleneck.

According to an eleventh aspect of the present invention, in the biomolecule analyzer of the above-mentioned tenth aspect, a second concave part is provided to the buffer solution tank at a position separated by a certain distance in the conveying direction from the first concave part, and the electrode is disposed at the second concave part.

According to the above-mentioned configuration, it is possible to prevent, by way of the second concave part, bubbles generating from the electrode during electrophoresis from spreading in the horizontal direction. In addition, at the inner side of the second concave part, it is possible to make microscopic bubbles generating from the electrode to agglomerate, and grow into larger bubbles. For this reason, it is possible to further prevent the bubbles generating from the electrode from migrating through the bottleneck formed by the first concave part and electrode cover towards the contact location between the transfer membrane and separation unit.

According to a twelfth aspect of the present invention, in the biomolecule analyzer of the above-mentioned tenth or eleventh aspect, the electrode cover includes a convex part that hangs down towards the first concave part.

According to the above-mentioned configuration, it is possible to further prevent, by way of the convex part, bubbles generating from the electrode from migrating along the bottom face of the electrode cover towards the contact location between the separation unit and transfer membrane.

According to a thirteenth aspect of the present invention, in the biomolecule analyzer of the above-mentioned twelfth aspect, the convex part of the electrode cover consists of a plurality of convex parts, the first concave part of the buffer solution tank consists of a plurality of concave parts, and the plurality of convex parts is disposed so as to individually hang down to the plurality of concave parts.

According to the above-mentioned configuration, it is possible to further prevent, by way of the plurality of convex parts, bubbles generating from the electrode from migrating along the bottom face of the electrode cover towards the contact location between the separation unit and transfer membrane.

According to a fourteenth aspect of the present invention, in the biomolecule analyzer of the above-mentioned tenth or eleventh aspect, an end part of the electrode cover is movably inserted in the first concave part.

According to the above-mentioned configuration, it is possible to further prevent bubbles generating from the electrode from migrating through the bottleneck formed by the end of the electrode cover and the first concave part towards the contact location between the transfer membrane and separation unit.

In addition, according to a fifteenth aspect, in the biomolecule analyzer of the above-mentioned twelfth or thirteenth aspect, the convex part of the electrode cover is movably inserted in the first concave part.

According to the above-mentioned configuration, it is possible to further prevent bubbles generating from the electrode from migrating through the bottleneck formed by the convex part of the electrode cover and the first concave part towards the contact location between the transfer membrane and separation unit.

According to a sixteenth aspect of the present invention, in the biomolecule analyzer of any of the above-mentioned tenth to fifteenth aspects, the first concave part is provided at a lower part of an end part of the contact location on a side of the electrode.

According to the above-mentioned configuration, it is possible to prevent the electric line of force arising from the contact location of the separation unit during electrophoresis from spreading at the electrode side. As a result thereof, the separability of analyte can be improved.

According to a seventeenth aspect of the present invention, in the biomolecule analyzer of any of the above-mentioned tenth to sixteenth aspects, a face of the electrode cover that opposes the buffer solution tank slopes relative to the conveying direction, and an end part of the face opposing the buffer solution tank that is farther from the contact location is farther from the electrode in a direction orthogonal to an in-plane direction of the transfer membrane, than an end part of the electrode cover that is closer to the contact location.

According to the above-mentioned configuration, it is possible to set free bubbles generating from the electrode in a direction distancing from the contact location.

According to an eighteenth aspect of the present invention, in the biomolecule analyzer of any of the above-mentioned tenth to seventeenth aspects, the electrode cover has a side wall that widens towards a bottom face of the buffer solution tank along two sides that are parallel to the conveying direction.

According to the above-mentioned configuration, it is possible to prevent bubbles generating from the electrode from migrating towards the contact location between the transfer membrane and separation unit from two sides of the electrode cover along the conveying direction of the transfer membrane.

According to a nineteenth aspect of the present invention, in the biomolecule analyzer of any of the above-mentioned tenth to eighteenth aspects, a water contact angle of a surface of the electrode cover is no more than 90°.

According to the above-mentioned configuration, it is possible to further facilitate setting free bubbles generating from the electrode along the surface of the electrode cover.

The present invention is not to be limited to the aforementioned respective embodiments, with various modifications within the scope shown in the claims being possible, and embodiments achieved by appropriately combining the technical means disclosed in each of the different embodiments are also included in the technical scope of the present invention. Furthermore, it is possible to form novel technical features by combining the technical means disclosed in each of the respective embodiments.

INDUSTRIAL APPLICABILITY

The present invention can be suitably employed in a two-dimensional electrophoresis apparatus.

EXPLANATION OF REFERENCE NUMERALS 1 transfer membrane
2 frame 10 framed transfer membrane
20 clamp
32 anode (electrode)
35 anode cover (electrode cover)
36, 37 electric line of force
38 constricting member (second insulating member)
41 cathode
50 electrophoresis gel chip (separation unit)
50a dispensing part
52 separation gel
70 slit
71 opening
72 electric line of force
73 upright member (first insulating member)
74 slit
101 transfer membrane
130 anode buffer tank (buffer solution tank)
130a, 130a' first concave part
130b second concave part
132 anode (electrode)
135, 136, 137, 138 anode cover (electrode cover)
135a end (end part)
136a, 137a, 137a', 138a, 138a' convex part
141 cathode
150 electrophoresis gel chip (separation unit)
150a dispensing part
152 separation gel
200, 201, 202, 203, 204, 205 biomolecule analyzer

The invention claimed is:

1. A biomolecule analyzer, comprising:
a transfer membrane;
a conveying unit that conveys the transfer membrane along a predetermined conveying direction;
a separation unit that perpendicularly abuts the transfer membrane and is installed vertically, separates analyte by way of electrophoresis, and dispenses the analyte that has been separated to the transfer membrane;
an electrode that is disposed at a position separated by a certain distance in the conveying direction from a contact location at the dispensing part between the separation unit and the transfer membrane; and
an insulating electrode cover that is disposed at an upper part of the electrode to abut the electrode or be separated from the electrode, wherein the insulating electrode cover is arranged so that it will constrict an electrical line of force between the electrode and the contact location at the dispensing part during electrophoresis and dispensing of separated analyte onto the transfer membrane.

2. The biomolecule analyzer according to claim 1, wherein one end part of the electrode cover is at a lower part of an end part of the contact location on a side of the electrode.

3. The biomolecule analyzer according to claim 2, further comprising a buffer tank in which the electrode is disposed, wherein a slit is formed between the one end part of the electrode cover and a bottom face of the buffer tank.

4. The biomolecule analyzer according to claim 1, further comprising a buffer tank in which the electrode is disposed, wherein the electrode cover is curved to a side of the electrode at a lower part of an end part of the contact location on a side of the electrode, so that one end part of the electrode cover is positioned at a lower part of the electrode, and
wherein a slit is formed between the one end part of the electrode cover and a bottom face of the buffer tank.

5. The biomolecule analyzer according to claim 1, further comprising a first insulating member that is disposed perpendicularly relative to the transfer membrane at a lower part of an end part of the contact location on a side of the electrode,
wherein the electrode cover is extended until an upper part of the first insulating member, and
wherein a slit is formed between the electrode cover and the first insulating member.

6. The biomolecule analyzer according to claim 1, further comprising, at
a lower part of an end part of the contact location on an opposite side to the side of the electrode,
a second insulating member that is disposed perpendicularly relative to the transfer membrane.

7. The biomolecule analyzer according to claim 1, wherein the electrode cover slopes relative to the conveying direction, and an end part of the electrode cover that is farther from the contact location is farther from the electrode in a direction orthogonal to an in-plane direction of the transfer membrane, than an end part of the electrode cover that is closer to the contact location.

8. The biomolecule analyzer according to claim 1, wherein the electrode cover slopes relative to a direction that is orthogonal to the conveying direction and parallel to an in-plane direction of the transfer membrane.

9. The biomolecule analyzer according to claim 1, wherein a water contact angle to a surface of the electrode cover is no more than 90°.

10. A biomolecule analyzer, comprising:
a buffer solution tank;
a transfer membrane that is disposed inside the buffer solution tank;
a conveying unit that conveys the transfer membrane along a predetermined conveying direction;
a separation unit that perpendicularly abuts the transfer membrane and is installed vertically, separates analyte by way of electrophoresis, and dispenses the analyte that has been separated to the transfer membrane;
an electrode that is disposed at a position separated by a certain distance in the conveying direction from a contact location at the dispensing part between the separation unit and the transfer membrane; and
an insulating electrode cover that is disposed between the electrode and the contact location,
wherein a first concave part is provided at a position on a bottom part of the buffer solution tank that is interposed by the electrode and the contact location, and
wherein the electrode cover hangs down towards the first concave part, and wherein the electrode cover is arranged so that it will constrict an electrical line of force between the electrode and the contact location at the dispensing part during electrophoresis and dispensing of separated analyte onto the transfer membrane.

11. The biomolecule analyzer according to claim 10, wherein a second concave part is provided to the buffer solution tank at a position separated by a certain distance in the conveying direction from the first concave part, and
wherein the electrode is disposed inside the second concave part.

12. The biomolecule analyzer according to claim 10, wherein the electrode cover includes a convex part that hangs down towards the first concave part.

13. The biomolecule analyzer according to claim 12, wherein the convex part of the electrode cover consists of a plurality of convex parts, wherein the first concave part of the buffer solution tank consists of a plurality of concave parts, and wherein the plurality of convex parts are disposed so as to individually hang down to the plurality of concave parts.

14. The biomolecule analyzer according to claim 12, wherein the convex part of the electrode cover is movably inserted in the first concave part.

15. The biomolecule analyzer according to claim 10, wherein an end part of the electrode cover is movably inserted in the first concave part.

16. The biomolecule analyzer according to claim 10, wherein the first concave part is provided at a lower part of an end part of the contact location on a side of the electrode.

17. The biomolecule analyzer according to claim 10, wherein a face of the electrode cover that opposes the buffer solution tank slopes relative to the conveying direction, and wherein an end part of the face opposing the buffer solution tank that is farther from the contact location is farther from the electrode in a direction orthogonal to an in-plane direction of the transfer membrane, than an end part of the electrode cover that is closer to the contact location.

18. The biomolecule analyzer according to claim 10, wherein the electrode cover has a side wall that widens towards a bottom face of the buffer solution tank along two sides of the electrode cover that are parallel to the conveying direction.

19. The biomolecule analyzer according to claim 10, wherein a water contact angle of a surface of the electrode cover is no more than 90°.

* * * * *